United States Patent [19]
Karkanen

[11] Patent Number: 5,839,901
[45] Date of Patent: Nov. 24, 1998

[54] INTEGRATED WEIGHT LOSS CONTROL METHOD

[76] Inventor: Kip M. Karkanen, 256 Castle Glen Rd., Walnut Creek, Calif. 94595

[21] Appl. No.: 943,043

[22] Filed: Oct. 1, 1997

[51] Int. Cl.⁶ .................................................. G06F 19/00
[52] U.S. Cl. ..................... 434/127; 600/300; 128/921; 434/127
[58] Field of Search ............................ 600/300; 128/920, 128/921; 235/114; 434/127; 364/709.03; 250/215; 482/1–9, 148, 900–902; 73/379.01

[56] References Cited

U.S. PATENT DOCUMENTS

| | | | |
|---|---|---|---|
| 4,192,000 | 3/1980 | Lipsey | 364/415 |
| 4,212,079 | 7/1980 | Segar et al. | 364/900 |
| 4,344,142 | 8/1982 | Diehr, II et al. | 364/473 |
| 4,766,539 | 8/1988 | Fox | 364/401 |
| 4,894,793 | 1/1990 | Ikemoto et al. | 364/709.03 |
| 4,951,197 | 8/1990 | Mellinger | 600/300 |
| 4,954,954 | 9/1990 | Madsen et al. | 364/413.29 |
| 5,173,588 | 12/1992 | Harrah | 235/114 |
| 5,412,564 | 5/1995 | Ecer | 600/300 |

FOREIGN PATENT DOCUMENTS

| | | | |
|---|---|---|---|
| 6304276 | 1/1994 | Japan | A63B 69/00 |

OTHER PUBLICATIONS

V. Antonetti, "The Equations Governing Weight Change in Human Beings" The American Journal of Clinical Nutrition, vol. 26 Jan. 1973.

Ainsworth et al. "Compendium of Physical Activities: classification of energy costs of human physical activities" Medicine & Science in Sports and Exercise vol. 25 pp. 71–80, 1993.

*Primary Examiner*—Glenn Richman
*Attorney, Agent, or Firm*—Gene Scott—Patent Law & Venture Group

[57] ABSTRACT

An integrated system of collecting data and reporting results, enabling an understanding of weight control and weight loss. The first embodiment of the invention is for a method of estimating an individual's baseline normal activities calories. The second embodiment of the invention is a method for the individual to plan and forecast weight loss goals. The third embodiment of the invention enables the individual to record estimates of weight and food calories and exercise calories constructing his own weight loss database. The individual's calories density is measured and is used to increase plan and forecast accuracy. A graphical representation of the data enables the individual to detect body water shifts, weight plateauing and resting metabolic rate changes so as to enable the individual to know the reasons why the individual is losing or not losing weight. The system organizes the data to minimize the impact of errors in the data while maximizing the data's information value. The system uses the individual's own body in a closed loop approach as its own calorimeter.

20 Claims, 17 Drawing Sheets

NORMAL ACTIVITIES

| WEEKDAY (HOURS) | WEEKEND (HOURS) | WEEKEND (CAL/DAY) | WEEKEND (CAL/DAY) | TOTAL (CAL/DAY) | (CAL/MIN) | RMR (XRMR) | (CAL/DAY) |
|---|---|---|---|---|---|---|---|
| 23.0 | 23.0 | 26.47 | 2772 | 2681 | 1.9 | 1.5 | 1813 |
| 80 | 84 | 50 | 52 | 20 ENTER 68 | 70 | 66 | 34 |

22 SEX  M  (M,F)

AGE (YRS)  35  (MAX 60, MIN 17)

24

CLOTHED WEIGHT (LBS)  180  (MAX 300, MIN 100)

26         26

HEIGHT   5 (FT.)    10 (IN) (MAX 7FTT., MIN 5FT.)

——— ENTER ——— CALC ———

|  | WEEKDAYS | WEEKENDS | TOTAL |
|---|---|---|---|
| 36 |  |  |  |
| NUMBER OF DAYS/ WEEK | 5 | 2 | 7 (EQUAL 7) |

42

NORMAL ACTIVITIES

| ACTIVITIES | MULTIPLE (xRMR) | WEEKDAYS (HRS/DAY) | WEEKENDS (HRS/DAY) | TIME (HRS/DAY) | TOTAL (CAL/DAY) | (CAL/MIN) |
|---|---|---|---|---|---|---|
| SLEEPING | 0.9 | 8.0 | 8.0 | 8.0 | 1.1 | 544 |
| OFFICE WORK - ACTIVE | 1.7 | 9.0 |  | 6.4 | 2.1 | 825 |
| WALKING - AVERAGE | 4.1 | 1.5 | 1.5 | 1.5 | 5.2 | 465 |
| SITTING - WATCHING T.V. | 1.2 | 1.2 | 3.0 | 1.7 | 1.5 | 155 |
| DRIVING - AUTOMOBILE | 1.5 | 1.5 | 1.3 | 1.4 | 1.9 | 163 |
| SITTING - EATING — 86 | 1.5 | 1.8 | 2.0 | 1.9 | 1.9 | 210 |
| MOWING LAWN - POWER | 4.5 | 40 | 1.0 | 0.3 | 5.7 | 97 |
| SWEEPING SIDEWALK | 4.0 |  | 0.2 | 0.1 | 5.0 | 17 |
| SITTING - READING | 1.2 |  | 1.0 | 0.3 | 1.5 | 26 |
| LIGHT ACTIVITY | 1.7 |  | 3.0 | 0.9 | 2.1 | 110 |
| OTHER | 1.6 |  | 2.0 | 0.6 | 2.0 | 69 |
|  |  |  |  | 0.0 | 0.0 | 0 |
|  |  |  |  | 0.0 | 0.0 | 0 |
|  |  |  |  | 0.0 | 0.0 | 0 |
|  |  |  |  | 0.0 | 0.0 | 0 |
| TOTAL | 1.5 | 23.0 | 23.0 | 23.0 | 1.9 | 2681 |
|  | 66 | 80 | 84 | 82 | 70 | 68 |

(38 above 2.0 column; 44 above 1.9; 74 above 1.9; 58 above 210; 54 at right)

FIGURE 17

WEIGHT LOG

| BEGIN No.DAYS | FOOD | AVERAGE EXERCISE | (CAL/DAY) NORMAL | ACTUAL DEFICIT | WEIGHT LOG (LBS/DAY) | (LBS/WK) | DENSITY (CAL/LBS) |
|---|---|---|---|---|---|---|---|
| 9 | 1900 | 617 | 2667 | 1384 | -0.51 | -3.57 | 2711 |
| 164 | 166 | 168 | 170 | 172 | 180 | 182 | 184 |

IF YOU PLAN TO LOSE WEIGHT COMPLETE NORMAL ACTIVITIES AND ENTER YOUR PLAN

|  | ENTER | VALUE 66 | SECTION |
|---|---|---|---|
| BEGIN WEIGHT (LBS) | 182.0 — 88 | | |
| MULTIPLE (xRMR) | 1.5 — 90 | 1.5 | NORMAL ACTIVITIES |
| BEGIN NORMAL ACTIVITIES (CAL\DAY) | 2681 — 92 | 2681 | NORMAL ACTIVITIES 68 |

— CALC —

|  | ENTER | END WEIGHT | DEFICIT |
|---|---|---|---|
| NUMBER OF DAYS | 94 — 30 | 171.6 — 114 | 1019 — 112 |
| AVERAGE FOOD (CAL/DAY) | 2000 — 96 | | |
| AVERAGE EXERCISE (CAL/DAY) | 400 — 98 | | PLAN/FORCAST |
| CALORIE DENSITY (CAL/LB) | 2935 — 100 | CALC | |
| AVERAGE NOMINAL (CAL/DAY) | 2619 — 106 | 2619 — 108 | |

WEIGHT LOG

| | ENTER | | | | CALCULATED | | ACTUAL |
|---|---|---|---|---|---|---|---|---|
| ACTIVITIES | BEGIN WEIGHT (LBS) | FOOD (CAL) | EXERCISE (CAL) | DAY | DAILY DEFICIT (CAL) | DAILY CHANGE (LBS) | ENDING WEIGHT FORECAST (LBS) | PLAN (LBS) |
| 6/1/95 | 182.0 | 1800 | 788 | 1 | 1669 | -0.57 | 181.4 | 181.7 |
| 6/2/95 | | 2100 | 824 | 2 | 1400 | -0.48 | 181.0 | 181.3 |
| 6/3/95 — 116 | /138 | 2200 | /122 | 3 | 473 | -0.16 | 180.8 | 181.0 |
| 6/4/95 | 179.0 | 1500 | /124 | 4 /120 | 1171 /132 | -0.40 /136 | 178.6 /146 | 180.6 |
| 6/5/95 | | 1700 | 693 | 5 | 1661 | -0.57 | 178.0 | 180.3 |
| 6/6/95 | 180.8 | 1900 | 709 | 6 | 1473 | -0.50 | 180.3 150 | 179.9 |
| 6/7/95 | | 1650 | 830 | 7 | 1840 | -0.63 | 179.7 | 179.6 |
| 6/8/95 | | 2400 | 768 | 8 | 1023 | -0.35 | 179.3 | 179.2 |
| 6/9/95 | 178.0 | 1850 | 945 | 9 | 1747 | -0.60 | 177.4 | 178.9 |
| | | | | 0 | 0 | 0.00 | 0.0 | 0.0 |
| | | | | 0 | 0 | 0.00 | 0.0 | 0.0 |
| | | | | 0 | 0 | 0.00 | 0.0 | 0.0 |

FIGURE 18

INTEGRATED WEIGHT LOSS CONTROL METHOD

BACKGROUND OF THE INVENTION

1. Field of the Invention

This invention relates generally to weight loss diets, and more particularly to a computational method and program to provide an integrated closed loop planning, forecasting and control system for individuals losing weight. It permits realistic daily weight loss planning and provides an integrated database for control of the individual's weight and all of the individual's estimated food, exercise and normal activity calories. The individual's calorie density is directly measured and is used to reduce errors in the data and is used to tell the individual how accurately the individual is estimating calories. The system separates out the individual's true weight loss from the individual's body water shifts, weight plateauing and the individual's changes in resting metabolism. It also provides the flexibility individuals need to change his or her goals, timing and adherence patterns while still maintaining control optimizing the individual's weight loss.

2. Description of the Prior Art

About 30% of Americans are currently trying to lose weight. Americans are experienced with weight loss. The average American female has been on about 6 diets and the average American male about 3 diets. About 90% of people who lose weight use their own do-it-yourself systems rather than commercial weight loss programs. The techniques they use to lose weight are primarily diet and/or exercise.

The American College of Sports Medicine recommends:

Lose no more the 2 lbs per week

Don't consume less than 1200 of food calories per day

Don't allow the calorie deficit to become greater than 1000 calories/day

Exercise between 20 to 60 minutes per session, 3 to 5 times a week and burn at least 300 calories per session The longer you exercise per session and the more sessions you have per week, the greater your weight loss will be The dropout rate of weight loss programs is quite high. About 80% of individuals in formal weight loss programs fail to achieve their targeted weight loss. Another study recently showed that 80% of a group of obese individuals could not lose 10% or more of their initial body weight.

The principal reasons for failure are unrealistic expectations, too much effort, expense, inconvenience and requiring too much time. An overriding reason is lack of results. Individuals need results in the short run to reassure themselves about their commitment to the long run.

Many of the physiological reasons for the failure of individuals to lose weight are largely unknown. Almost all experts agree that calorie deficits are required to lose weight. Yet present tools used outside of the scientist's laboratory are inadequate. To determine the physiological reasons for weight loss, a weight loss method must be able to identify and separate out all of the major physiological variables and track these variables within a mathematically consistent and physiologically consistent thermodynamic model where all calories and weight changes are accounted for and balanced.

Weight loss requires time, patience and focus. Sustainable weight loss takes weeks to months to achieve and it is easy to lose control over these time frames. Although there are plenty of diet foods and exercise schemes and software available to lose weight, there are no complete physiologically consistent thermodynamically balanced control tools available which takes the results of a free living individual's calories and weight changes and systematically uses these results to analyze, report and control the individuals' weight loss experience as a closed loop system.

Current tools used to estimate individual weight loss are crude, inaccurate and insensitive. Most are incapable of minimizing errors in the input data thereby providing output containing the same errors.

Current tools all convert calories to weight using a constant calorie density of 3500 Cal/lb.

The 3500 Cal/lb is derived from groups of people and assumes a constant mix of carbohydrates, protein and fat are burned. The 3500 Cal/lb, measured in a scientist's laboratory, is derived given perfect information about the caloric content of carbohydrates, protein and fats. For free living individuals who are constantly burning different mixes of carbohydrates, proteins and fat, the assumption of constant mix is unrealistic. Additionally, free living individuals who estimate calories to lose weight do not have perfect calorie information. Their calorie estimates contain unknown errors. The assumption of perfect information about calories is also unrealistic. The calorie density of 3500 Cal/lb is a useful theoretical baseline in a perfect information environment but individuals on a weight loss program will incur their own calorie densities which will vary from about 2000 Cal/lb to 10,000 Cal/lb or more. Current tools using 3500 Cal/lb as the calorie density are applicable in a perfect information environment but less applicable in a noisy less then perfect environment of free living individuals.

Current tools are also incapable of separating out the individual's body water shifts, weight plateauing and changes in the individual's resting metabolism which all may occur during a weight loss program. These are distinctly different physiological phenomena which interfere with individual weight loss and which require different actions be taken.

Current tools forecasting ending weight are often grossly inaccurate leading to unrealistic expectations regarding the amount and timing of weight loss. These unrealized expectations impede the individual's weight loss program. Moreover, some tools are unnecessarily rigid in controlling weight loss requiring specific types and quantities of food to be consumed within specific time frames.

The present invention focuses on errors in measurement of individual calorie estimates but does not exclude errors in weight measurements. The best and most accurate weighing scale is a doctor's balance beam scale. Most modern home weighing scales measure absolute weight reasonably accurately within ±2%. The repeatability of home weighing scales measurements (i.e. measuring the same weight the same everytime) is about ±0.5% and is more important for individuals on a weight loss program looking to measure small changes in weight. The present invention uses cumulative weight loss across time. As time increases, errors in weight measurements decrease minimizing random weight measurement errors. Any errors in weight measurements are comprehended by this invention and have the same impact as errors in individual calorie estimates.

The present invention can also be used for individuals who wish to gain weight. However, since 90% of those individuals who want to change their weight want to lose weight, focus is directed to losing weight.

As seen in FIG. 1, weight loss is a closed loop system consisting of a few key variables of time, weight, food calories, exercise calories, normal activities calories and calorie density. The individual creates a calorie deficit by diet and/or exercise and the individual's body responds by converting body weight into energy in a thermodynamically balanced system. The individual's calorie density is a measuring gauge for how this closed system is working. Calorie density represents the individual's efficiency of losing weight or the necessary calories burned to lose a pound of body weight.

Individual weight loss is a highly individual experience. There is a great deal of variation between individuals. The physiological rules that apply to groups of people often times may not apply to individuals. Individuals use different mixes of food and exercise. Individuals count calories differently, incur different kinds of body water shifts and weight plateauing and have different resting metabolic rate reactions to diet and exercise. Individuals also have different time constraints and different lifestyles in which to fit their weight loss program. Without a structured and systematic view of these weight loss variables, it is difficult for an individual to isolate each variable and determine the impacts of each on his or her weight loss program. And without maximum flexibility, it is difficult for individuals to fit their weight loss program into their weight loss system with constantly changing lifestyle priorities Weight loss data are also noisy and difficult to interpret. Dieter's who estimate calories do not know how their calorie estimates specifically impact their weight changes nor are they aware of the magnitude and impact of the random and systematic errors intrinsic to their estimates. Those who do estimate food calories typically systematically underestimate them by 15% to 25% or more. Constant caloric deficits cause more constant weight changes while more variable caloric deficits tend to cause more variable weight changes. On average, individuals in equilibrium with their weight will experience random oscillations of their weight of about ±2 lbs on any given day due to body water shifts. During calorie deficits, weight fluctuations are likely to be more. Weight responses to calorie deficits, moreover, are oftentimes moderated by varying time lags in body water shifts. Oftentimes, body water shifts or weight plateauing cause weight to remain level or increase when weight is really decreasing causing the individual to terminate his or her weight loss program prematurely since short term body water shift oscillations and weight plateauing have no long term weight consequences. Finally, many individuals experience changes in their resting metabolic rates, which have no impact in the short run, but may increase, have no impact or decrease their long term rate of weight loss. A decreasing resting metabolic rate can significantly impact an individual's weight loss program.

Individuals want to lose weight quickly and comfortably. One successful weight loss strategy is to set the weight loss numbers, within the context of the individual's own lifestyle, so that the individual will lose weight and barely be aware of it. By so doing, the individual will lose weight both comfortably and optimally.

The purpose of this invention is to separate out and quantify all of these confounding factors while minimizing the noise impact and maximizing the information value of the individual's collected weight loss data. The individual can use the computer and his or her own personal weight loss method to manage and control weight loss comfortably. The individual can use readily available personal estimates of calories instead of exact values to achieve the same results. The individual can Plan and Forecast future weight loss accurately using these estimates validating weight loss expectations through actual weight loss results. And the individual can maintain control using this invention to tell why he or she is losing or not losing weight and what to do about it.

U.S. Pat. No. 4,192,000, issued on Mar. 4, 1980 to Elmer A. Lipsey discloses an electronic calorie counter which measures an individual's normal activities and exercise calories expended by sensing the vertical motion of the user and using general activity coefficients such as sedentary, light, moderate, vigorous and severe. The instant invention is distinguishable from the present invention in that it focuses only on normal and exercise calories, uses general activity coefficients and does not estimate changes in the individual's weight.

U.S. Pat. No. 4,212,079, issued on Jul. 8, 1980 to Richard B. Segar and C. Marascalco discloses a device which displays an individual's total food calorie intake or total calories expended in normal activities and/or exercise in real time. It is distinguished from the present invention in that the resulting totals do not estimate the individual's weight change as a result of the accumulated calorie totals.

U.S. Pat. No. 4,344,142, issued on Aug. 10, 1982 to James R. Diehr and Theodore A. Lutton discloses a computer controlled rubber processing feedback system. It is distinguished from the present invention in that the present invention concerns human weight loss.

U.S. Pat. No. 4,766,539 issued on Aug. 23, 1988 to Henry L. Fox discloses a system of future weather forecasting based on a data base of historical weather patterns. He uses a computer to forecast expected future trends and then is able to estimate insurance premiums for a client insuring against future weather conditions. The instant invention is distinguishable from the present invention in that the present invention concerns human weight loss.

U.S. Pat. No. 4,894,793 issued on Jan. 16, 1990 to Yutaka Ikemoto and Akiyoshi Yamashita discloses a device for retrieving specific foods and calories from a data base of foods. The instant invention is distinguishable from the present invention in that weight changes are not estimated.

U.S. Pat. No. 4,954,954 issued on Sep. 4, 1990 to Lamar R. Madsen discloses a device which estimates food calories from a menu of selected foods and is distinguishable from the present invention in that weight changes are not estimated.

Japanese Patent No. 06304276A issued on Jan. 11, 1994 to Morioka Shunichi discloses a device which accumulates food calories consumed and exercise calories expended and displays a calorie excess/shortage and is distinguishable from the present invention in that it does not use this information to estimate changes in the individual's weight.

A deterministic mathematical formulation of human weight loss by V. Antonetti in "The Equations Governing Weight Change in Human Beings," The American Journal of Clinical Nutrition, Vol. 26, No. 1, January 1973, estimates individual weight loss over time based on individual food and activity calories. It was not intended to be used to control an individual's weight loss program and it is not clear that it can be used to do so.

The formulation is quite complex and is difficult to use for several reasons. It requires that individual food calories, exercise calories and calorie density be constant. The formula uses the calorie density factor of 3500 Cal/lb as a constant even though it is known that, for individuals, this factor may be very different. The formula uses normal activity coefficients of sedentary, light, moderate, vigorous and severe which many individuals find difficult to define and apply to themselves resulting in less accuracy and loss of credibility. It also is an open loop estimate unable to process and use the daily feedback generated from the individual to control and/or update his or her weight loss process and using the results of this formula are likely to degenerate over time. Moreover, use of this formula, by itself, fails to recognize and deal with body water shifts, weight plateauing and resting metabolism shifts. Antonetti validates his equation using the results of groups of people. However, data from groups of people eliminates the problems of body water and resting metabolism changes as body water and resting metabolism changes tend to cancel each other out in groups of people but not in individuals. He also may have double counted the individual's Specific Dynamic Action (SDA) which is the number of calories the body expends digesting food and is about 7% to 10% of the food calories eaten. That is because, the activity coefficients he uses for normal activities are usually calculated for free living individuals without regard to their food consumption and generally includes the SDA effect in the activity coefficients already. Antonetti formulated the solution to determine the amount of time it would take to lose a specific amount of weight. It is not clear that other types of "what if" scenarios such as how much weight would be lost in a specific time has tractable solutions. Antonetti provides no generalized solution to his equation, only showing the results of using his formula. As seen in FIG. 2, a stand alone deterministic mathematical model of weight loss without integration with what the individual actually does, is naive and fails to capture all of the dynamics of actual weight loss.

There have been many different food and nutritional computer programs published over the years claiming to forecast and control individual weight changes. They include Diet Pro from Lifestyle Software, Sante from Hopkins Technology, Health & Diet from Software Solutions, The Diet Balancer from NutriData Software, Lifeform from Fitnesoft, and a family of weight loss software programs from Nutrigenie. Typically these products are food database programs and focus on increasing the accuracy of counting food calories using some variation of the generalized classical formulation:

$$W_t = W_0 - \Delta W \quad (1)$$

where:
$\Delta W = (\Delta F - \Delta E - \Delta N)/3500$ and:
$W_t$ = Weight (lbs) at time t
$W_0$ = Initial Weight (lbs) at time t=0
$\Delta W$ = Change in Weight (lbs)
$\Delta F$ = Change in Food Calories (Cal)
$\Delta E$ = Change in Exercise Calories (Cal)
$\Delta N$ = Change in Normal Activites Calories (Cal) where typically $\Delta N = 0$ where the individual's future weight is forecasted as the individual's initial weight plus the individual's forecasted total change in weight. Weight change in turn is equal to the individual's total change in calories, divided by the calorie density of 3500 Cal/lb. This classical model, strictly speaking, is most accurate as a point estimate for very small changes but it is used to forecast weight changes across much larger time frames with corresponding decreases in accuracy and increasing greater calorie imbalances.

All of these software products do not systematically integrate the classical formulation into their actual weight loss system. Rather, the forecast is performed independent of what the individual actually does, leaving it up to the individual to discern differences from the forecast. Only some and not all of the key physiological variables are used by the classical model making it difficult for the individual to understand the reasons for his or her weight loss variance.

Most of these software programs assume that individual's change in normal activity calories due to changes in weight is negligible or zero. Some use generalized activity coefficients such as sedentary, light, moderate, vigorous and severe which are difficult to define and apply to individuals and introduce systematic errors into the ending weight estimates.

In addition, the classical formulation assumes everybody loses weight at a constant calorie density of 3500 Cal/lb creating an open loop system. This assumption may or may not be true and depends upon the individual's actual calorie density which is neither explicitly measured nor used. By using a constant 3500 Cal/lb for all individuals, errors in calorie estimates or weight measurements are systematically introduced into the weight loss estimates rather than minimized resulting in weight loss forecasts as much as 2 times or more greater than actual. Such large error rates are unsuitable for weight control.

Finally, since most of these programs are food database programs, they direct the individual to focus on increasing the accuracy of their food calorie estimates. A singular and narrow concern with increasing the accuracy of food calorie estimates directs the individual's incremental energies and time toward an activity which has may have limited incremental benefits. Food calories are inherently difficult to estimate accurately. This focus is in part due to the inherent structure of the classical model itself which requires perfect information to work best. And because of all of the other limitations and insensitivities of the classical model, it is unclear that the individual's incremental efforts can be seen or are equally rewarded by the same incremental results. The present invention is distinguished from the classical model as it tells the individual whether he or she ought to spend his or her incremental energies and time increasing the accuracy of his or her calorie estimates.

Because of these limitation, the classical model oversimplifies the individual's actual weight loss process and contains sufficient calorie imbalances and inaccuracies to render it a less than satisfactory model for weight control.

The prior art teaches a wide variety of weight loss methods. However, the prior art does not teach a method providing the insight into the calorie cycle of the present approach so as to allow an accurate prediction of weight loss and an improved control over the process. The present invention fulfills these needs and provides further related advantages as described in the following summary.

SUMMARY OF THE INVENTION

Accordingly, several objects and advantages of my invention are:

The primary object of this invention is to provide the individual with a simple to use weight loss management tool to control weight loss more accurately and flexibly. The individual begins his or her weight loss program trying several food and exercise calorie deficit scenarios and recording the data before committing to his or her final weight loss Plan. Thereafter the individual uses said data and Plan, which reflects the individual's compromises between goals, comfort level and lifestyle, to lose weight optimally increasing his or her success rate.

A further object of this invention is to provide firstly, a database means for the individual to Plan and Forecast data about his or her weight loss goals and secondly said database means for the individual to record his or her actual data and thirdly, said database means to report his or her weight loss experience. Said database means offers a more realistic, flexible and accurate Planning, Forecasting and Control system than deterministic mathematical equations or classical weight loss modeling.

A further object of this invention is to provide an integrated system which consistently models and is sensitive to the individual's weight loss process daily, weekly and monthly.

A further object of this invention is to use a closed loop system to produce more accurate Plans and Forecasts of weight. In a closed loop system, Plan and Forecasted Ending Weight using data from the individual's said database will cancel most of the systematic errors contained within the input data.

A further object of this invention is to report and use the individual's own caloric density as a feedback measure of how this individual's closed loop system is operating. Calorie density tells the individual how efficiently he or she is losing weight. It also tells the individual about the accuracy of his or her calorie estimates. The greater the individual's actual calorie density deviations from 3500 Cal/lb, the less accurate is the individual's calories estimates.

A further object of this invention is to use said database means to separate out the individual's true weight loss from body water shifts, weight plateauing and resting metabolic changes.

A further object of this invention is to present this weight loss system as intuitive and simple, using diet and/or exercise, in the way most people are accustomed to thinking and acting when losing weight.

A further object of this invention is to use all of the known laws of human weight loss physiology to model individual weight loss consistently and to make weight loss more effective.

A further object of this invention is to highlight and focus on the actual weight loss experience of individuals and their weight loss idiosyncrasies in contrast to fitting said weight loss experience into group weight loss patterns and norms.

A further object of this invention is to permit the individual greater flexibility to vary daily food and exercise calories while still remaining in control. Greater flexibility permits easier interfacing with the individual's own lifestyle accommodating changes easily without loss of control.

A further object of this invention is to provide daily weight forecasts independent of actual daily weighings so the individual can view his or her forecasted weight without necessarily having to weigh himself or herself every day. Forecasted daily small incremental weight changes, which cannot be seen on the weight scales, motivate the individual to continue.

A further object of this invention is to allow the use of reasonable estimates of actual food and exercise calories rather than exact values thereby eliminating the additional effort of collecting more exacting calorie data and mitigating the ever present concern over calorie accuracy without necessarily losing weight loss effectiveness.

A further object of this invention is to provide said data base means for the individual to estimate his or her baseline daily actual normal activity calories significantly more easily and with more credibility than using general classifications such as light, moderate, heavy etc. which are less accurate when applied to individuals and lack credibility.

A further object of this invention is to provide said data base means for the individual to estimate his or her daily actual normal activity calories separately identifying the individual's resting metabolism.

A further object of this invention is to minimize random errors and accentuate longer term trends by using cumulative weight and calorie data appropriately. Such data aggregation is only effective in a closed loop system and will accentuate long term trends showing the individual why or why not he or she is losing weight.

A further object of this invention is to establish a calorie density upper control limit whereby calorie densities greater than about 6000 Cal/lb suggest that the individuals' calorie counting is too loose (absent significant excess body water shifts, weight plateauing or slowing resting metabolism).

A further object of this invention is to consistently maintain the mathematical relationships between daily point estimates such as daily weight, daily food calories, daily exercise calories, daily normal activity calories, daily calorie deficits and daily resting metabolic calories with average estimates such as average food calories, average exercise calories, average normal activity calories, average calorie deficits and average calorie density.

A further object of this invention is to define said point estimates and said average estimates so that Plan, Forecast and Actual point estimates and average estimates are defined exactly the same so that variances between Plan, Forecast and Actual estimates are pure and consistently defined.

A further object of this invention is to permit the individual to easily explore a variety of "what if" scenarios of the individual's key weight loss variables, permitting weight planning optimization.

A further object of this invention is to compensate for approximately a ±25% error rate in the individual's Food Calories, Normal Exercise Calories and Exercise Calories estimates to set a maximum level of food calories to be eaten by the individuals so he or she can begin to actually lose weight.

A further object of this invention is to approximately account for the individual's Specific Dynamic Action (SDA) effect by assuming that it is accounted for in the individual's estimate of Normal Activities since most of the activity coefficients probably include the SDA effect in them.

A further object of this invention is to minimize the data collection effort so that low cost, common everyday household appliances such as a weighing scale and home computer and common information sources such as food labels and food calorie booklets can be used effectively, in lieu of more expensive alternatives.

A further object of this invention is to allow the individual to enter and use his or her own resting metabolic rate to override the calculated value, thereby possibly increasing forecast accuracy and credibility.

A further object of this invention is to incorporate into the individual's Plan no resting metabolic changes (not explained by weight changes) since on average, physiological studies show groups of individuals' resting metabolic rates will not change while on a diet and/or exercise program. If the individual's resting metabolic rate does change, it will appear as a major deviation from the Plan.

A further object of this invention is to permit the individual to separate and highlight true weight loss from body water shifts, weight plateauing and resting metabolism shifts using a graphical display of the individual's weight changes.

A further object of this invention is to provide the ability for the individual to move the Plan graph and overlay it onto the individual's actual weight data changing some or all of the individual's key weight loss variables, graphically, so as to provide a means of producing a set of graphical solutions to the question of what Plan numbers are implied in the individual's actual weight data.

A further object of this invention is to provide the individual with sufficiently accurate data about his or her weight loss experience to uncover the main reasons why the individual is losing or not losing weight.

A further object of this invention is to provide the individual with effective solutions for the main reasons for not losing weight so the individual can make the proper decisions based on the right reasons.

A further object of this invention is a weight loss system applicable to human beings.

A further object of this invention is to obey and integrate all of the laws of thermodynamics and human physiology where energy and mass are conserved and mass is converted into energy and energy into mass.

A further object of this invention is to provide reports which interface with and are consistent with the weight loss recommendations of the American College of Sports Medicine.

A further object of this invention is to use the computer and current computer modeling techniques to accomplish these objects.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings:

FIG. 17 shows one embodiment of the input data needed and the resulting output used for calculating the individual's average daily normal activity calories.

FIG. 18 shows one embodiment of the input needed and the resulting output of an individual's weight loss planning, forecasting and control database system distinguishing between the Plan/Forecast section and the Actual section.

DETAILED DESCRIPTION OF THE PREFERRED EMBODIMENTS

Planning Individual Normal Activity Calories

Figure 3:
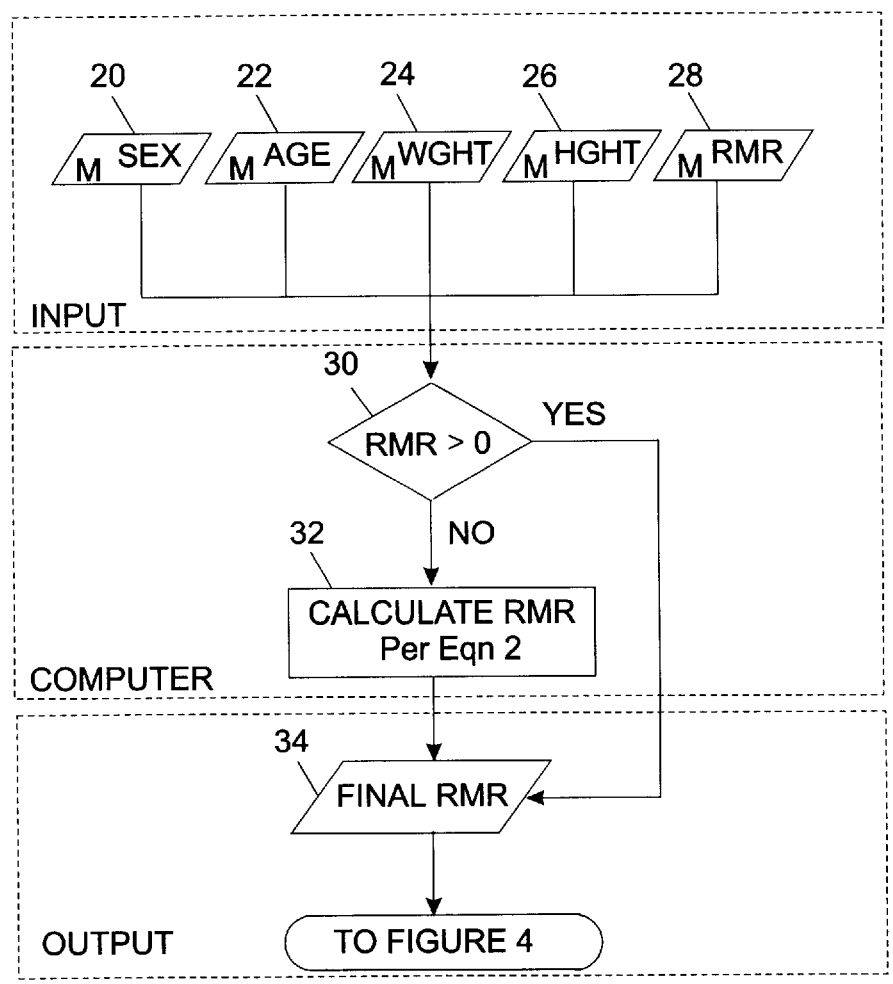
FIG. 3 is a detailed flow diagram showing how the system estimates individual resting metabolic rate including the capability to override the calculated value.

First, the individual estimates his or her daily resting metabolic rate. The individual enters his or her Sex 20, Age 22, Beginning Actual Weight 24 and Height 26 as seen in FIG. 3 and FIG. 17 where M in the flow diagrams means manual input by the individual. Final Plan Resting Metabolic Rate is calculated in accordance with the equations of Harris and Benedict as seen in Equation 2a and Equation 2b.

$$\text{Male } RMR = 66.47 + 13.75W + 5H - 6.755A \quad (2)(a)$$

$$\text{Female } RMR = 655.1 + 9.56W + 1.85H - 4.68A \quad (2)(b)$$

where:
RMR=Plan Resting Metabolic Rate (Cal/day)
W=Nude Beginning Actual Weight (kg) where $45 \leq W \leq 136$ kg
H=Barefoot Height (cm) where $152 \leq H \leq 213$ cm
A=Age (yrs) where $A \geq 17$ yrs and:
where 5 lbs for men and 3 lbs for women are subtracted from clothed weight to determine nude weight without loss of accuracy. The limits are approximate and are designed to exclude atypical body sizes where these formulas may not apply. Furthermore note the rate of change of RMR is See "A Biometric Study of Basal Metabolism in Man" by J. A. Harris and F. G. Benedict, Carnegie Institution, Washington, 1919.

The individual can override the calculated value by entering his or her own Actual Resting Metabolic Rate 28 as seen in FIG. 3. The computer calculates and displays the result Final RMR 34 in FIG. 3 and FIG. 17.

For example, the 35 year old, 180 lb, 5 ft 10 in male in FIG. 17 has an estimated resting metabolic rate of $66.47 + 13.75 \times [(180-5)/2.2] + 5 \times 70 \times 2.54 - 6.755 \times 35 = 1813$ Cal/day.

Figure 4:
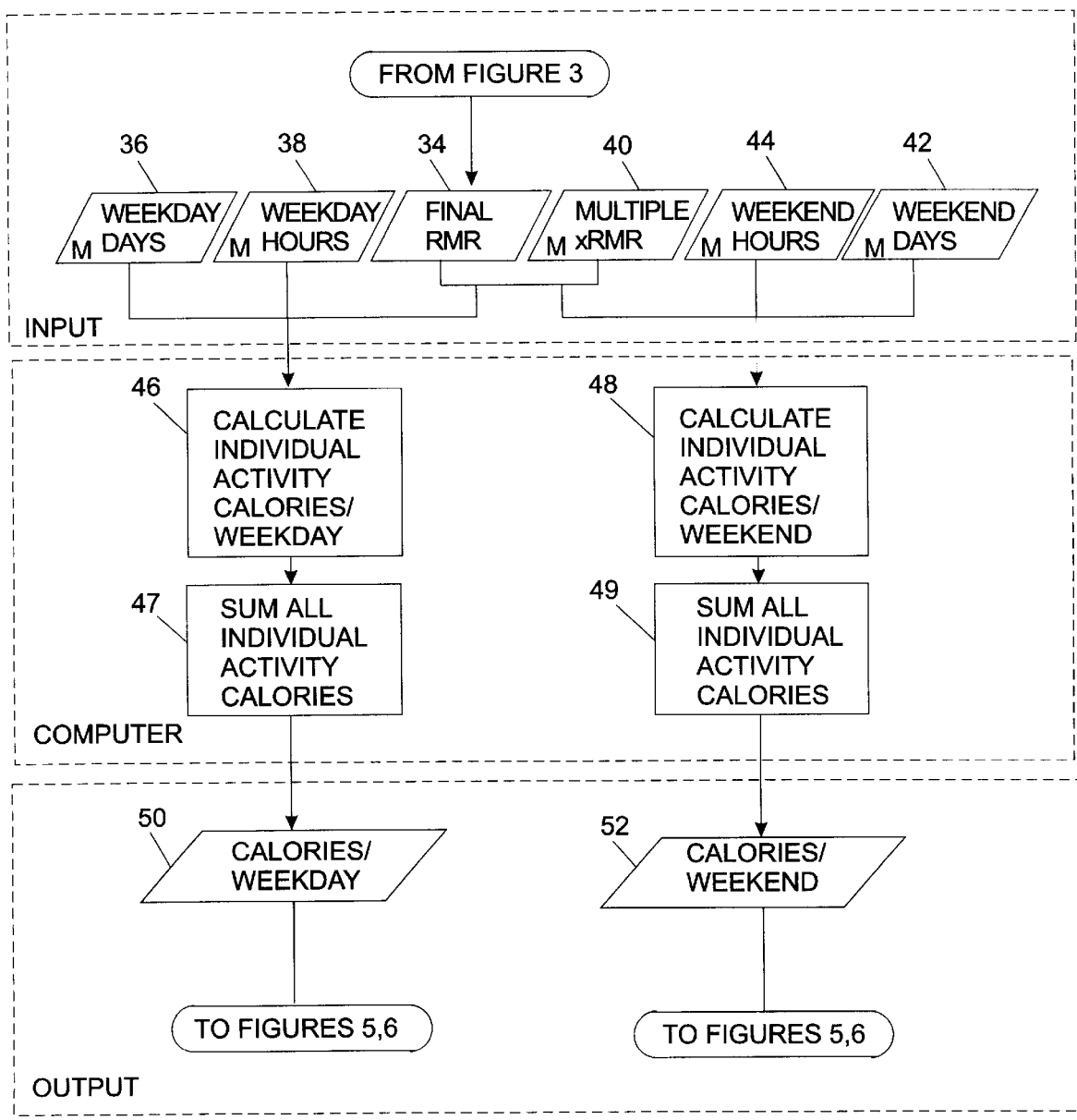
FIG. 4 is a detailed flow diagram showing how the system calculates the individual's weekday and weekend calories.

Next, the individual divides his or her typical week into Number of Weekday Days per Week 36 and Number of Weekend Days per Week 42 as seen in FIG. 4 and FIG. 17. Oftentimes activity patterns for weekday days differ from weekend days. Usually, a routine week is composed of 5 Number of Weekday Days per Week and 2 Number of Weekend Days per Week. If all days activities are the same, then there need be no distinction between weekday days and weekend days and either category can be used. The total of weekday days and weekend days must be seven days, the number of days in a week. The individual then enters a Description of Weekday Activities and a Description of Weekend Activities 86 for an average week as seen in FIG. 17. For each activity, the individual enters a corresponding Activity Coefficient Multiple (xRMR) 40 as seen in FIG. 4 and FIG. 17 representing a multiple of the individual's resting metabolic rate. See Table 1 for examples of some activity coefficients.

TABLE 1

Normal Activity Coefficients, Multiples of Resting Metabolic Rate

| Activity | Activity Coeff (xRMR) |
|---|---|
| Automobile Repair | 3.6 |
| Cleaning House | 3.5 |
| Driving - Automobile, Traffic | 2.4 |
| Light Activity | 1.7 |
| Sitting - Reading | 1.2 |
| Sleeping | 0.9 |

Also see "Compendium of Physical Activities: Classification of Energy Costs of Human Physical Activities" by B. E. Ainsworth et. al, in Medicine and Science in Sports and Exercise, Vol. 25, No. 1, 1993, pp. 71–80 for examples of other activity coefficients. The individual also enters an estimate of the number of Weekday Hours 38 or Weekend Hours 44 he or she spends on each particular activity as shown in FIG. 4 and FIG. 17.

All major activities should be listed. If the individual has an activity that is not listed on the table, he or she should pick an activity similar to it that is listed and estimate a value. If the individual has a variety of different activities every day that are difficult to summarize, the individual should describe all of these various activities as light, moderate or heavy and use that activity coefficient.

Figure 6:
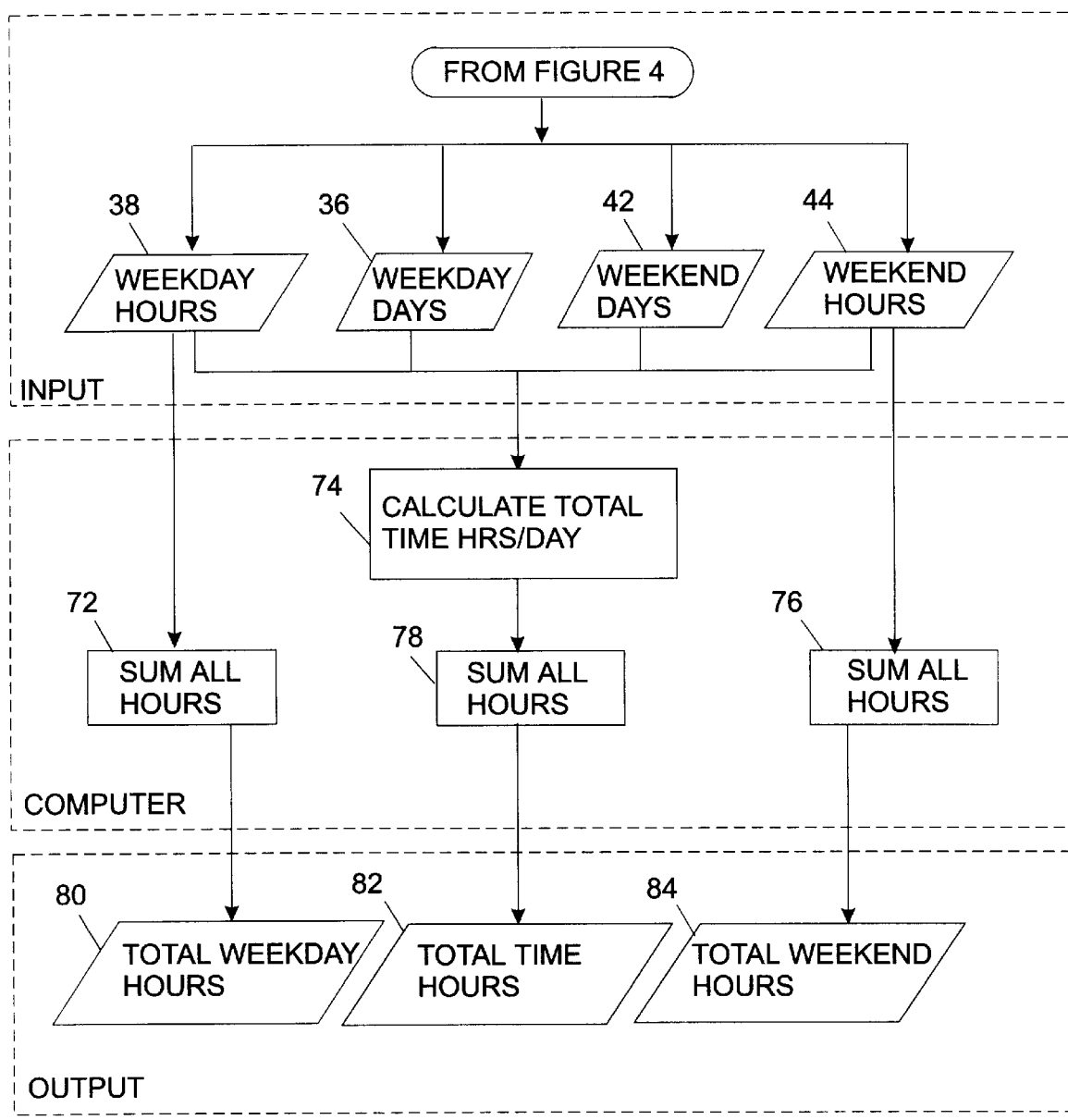
FIG. 6 is a detailed flow diagram showing how the system calculates the individual's total normal activity time from the individual's weekday and weekend hours.

The total number of Weekday Hours of activities 80 and Weekend Hours 84 is summed as seen in FIG. 6 and FIG. 17 and should be equal to 24 hours if the individual does not plan on exercising. If the individual plans on exercising, the total number of hours 80 and 84 should be less than 24 hours by the average number of hours/day/week that the individual plans on exercising. Exercise is excluded because it is accounted for separately. For example, if an individual plans on exercising 3 hours per week, the 24 hours should be reduced by 0.43 hours since on average the individual plans on spending this amount of time per typical day per week exercising.

Figure 5:
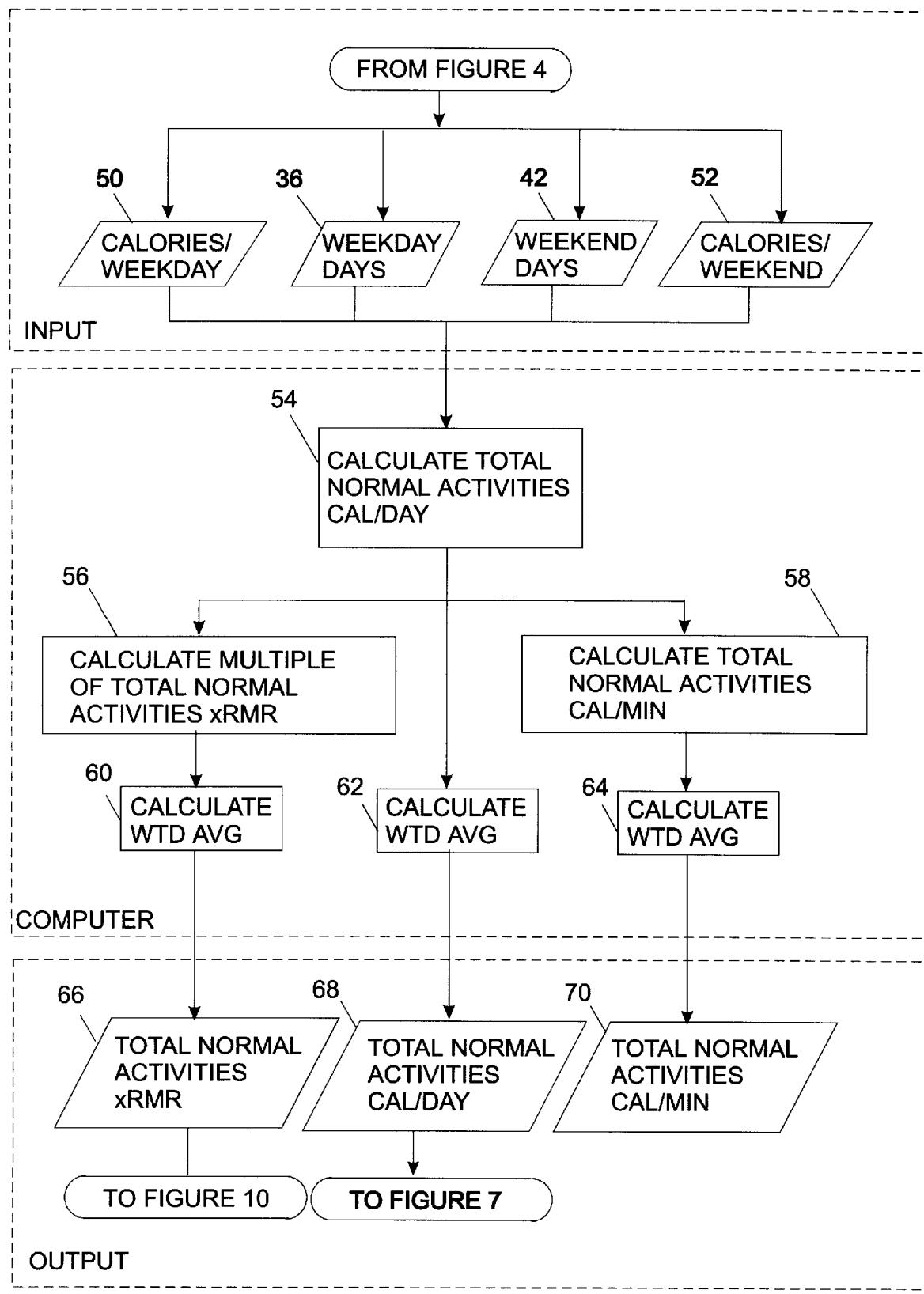
FIG. 5 is a detailed flow diagram showing how the system calculates the individual's normal daily activity calories.

The computer calculates the total weighted average number of calories the individual spends per average day on Plan Initial Normal Activity Calories 68 and the multiple of his or her estimated Plan Initial Normal Activity Calories Multiple of Resting Metabolic Rate (xRMR) 66 that his or her Plan Initial Normal Activity Calories 68 represent as seen in FIG. 5 and FIG. 17. The computer also calculates the individual's Plan Initial Normal Activity Calories in calories per minute 70 as seen in FIG. 5 and FIG. 17.

The individual's daily Plan Initial Normal Activity Calories 68 represents an average for any particular day. It is split between the individual's Weekday Calories 50 and Weekend Calories 52 seen in FIG. 4 and FIG. 17. For individuals who tend to have relatively uniform activity patterns, any particular day's actual normal activity calories expended would tend to be close to the estimated average. For individuals whose actual daily normal activity calories are more variable, the variance from the average would tend to be greater. However, cumulatively, over time, if the Plan Initial Normal Activity Calories 68 are reasonably accurate, the cumulative variances from actual should tend to cancel each other out trending toward the estimated average.

Forecast accuracy for the individual's Plan Initial Normal Activity Calories 68 is about ±0% to ±25% or more at 95% confidence limits.

For example, the 35 year old, 180 lb, 5 ft 10 in male in FIG. 17 has an estimated Plan Resting Metabolic Rate of 1813 Cal/day. His typical weekly activity pattern is divided between 5 Number of Weekdays per Week and 2 Number of Weekend Days per Week. His total Weekday Hours and total Weekend Hours is 23 hours as he plans on exercising 1 hour per day, everyday of the week. Using Office Work—Active, the time spent on office activity for a typical week is (5/7)×9=6.4 hours. The rate of calories office work burns per minute is (1.7)×(1813)/(24×60)=2.1 Cal/min. The total calories burned in office work in a typical week is then (6.4)× 60×2.1~825 Cal/day. For all activities, the individual's Plan Initial Normal Activity Calories of 2681 Cal/day is 2681/1813=1.5 times as great as the individual's Plan Initial Normal Activity Calories Multiple of Resting Metabolic Rate (xRMR) and is the same as 2681/(24×60)=1.9 Cal/min.

The individual's Plan Initial Normal Activity Calories 68 and Plan Initial Normal Activity Calories Multiple of Resting Metabolic Rate (xRMR) 66 are carried over as input into the Weight Log section as seen in FIG. 18.

The format shown in FIG. 17 is not limiting and can display in many other different formats.

This technique is more advantageous than directly estimating food calories because the individual's normal activities calories are usually more stable, better known and less variable than food calories. Furthermore, average normal activity calories can be estimated, a priori, within a few minutes, using a computer, rather than counting food calories which takes weeks of effort.

This technique is also more advantageous than requiring the individual to estimate his Plan Initial Normal Activity Calories each day which is time consuming and which most individuals would find onerous and which may have marginal benefits.

This technique is also more accurate and credible than using generalized activity coefficients such as light, moderate, heavy, vigorous and severe. This technique explicitly shows and accounts for the individual's resting metabolic rate separately.

Planning Weight Loss before Beginning a Weight Loss Program

Figure 7:
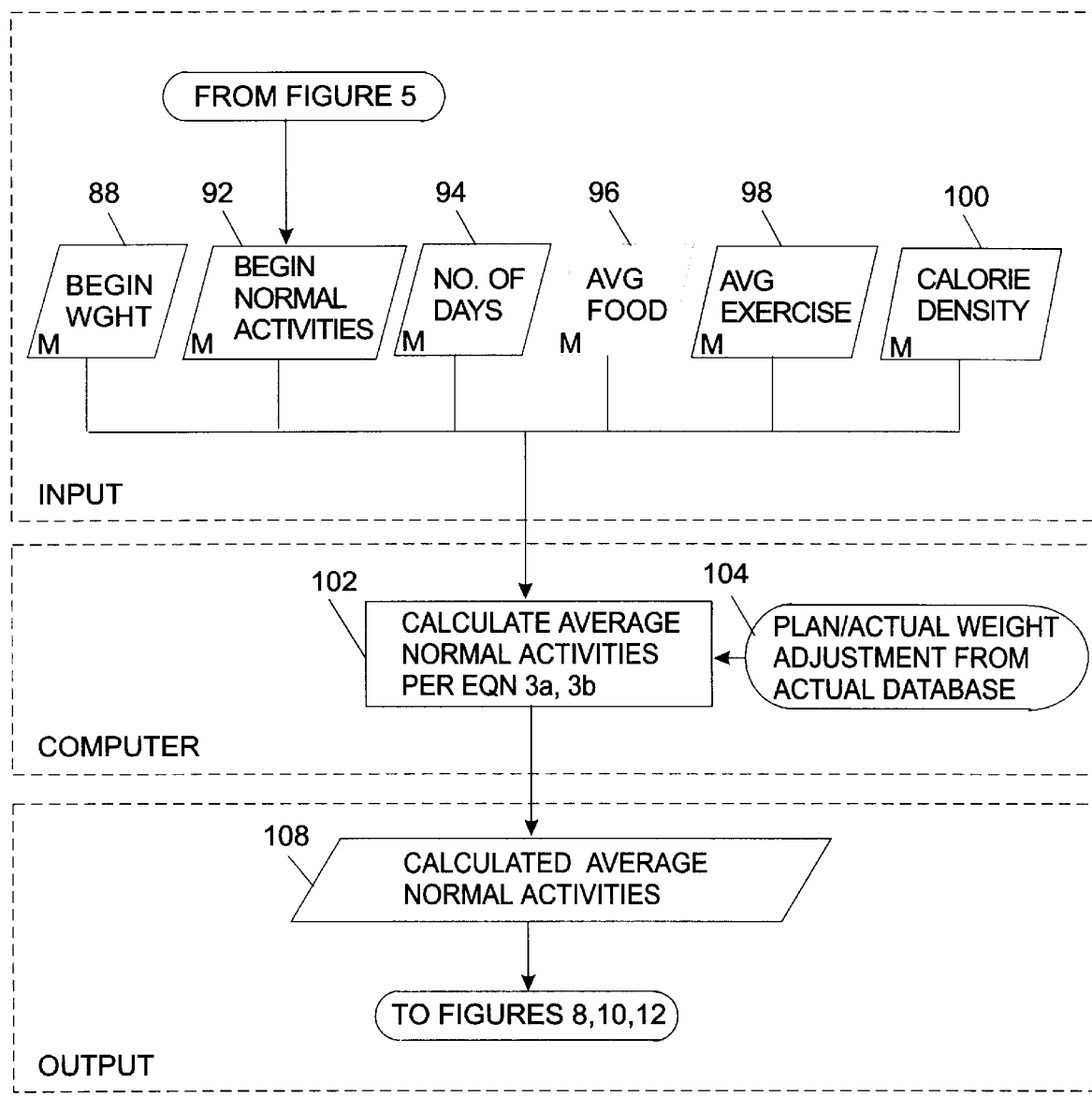
FIG. 7 is a detailed flow diagram showing how the system calculates the individual's calculated normal activities from Plan/Forecast input data.
Figure 8:
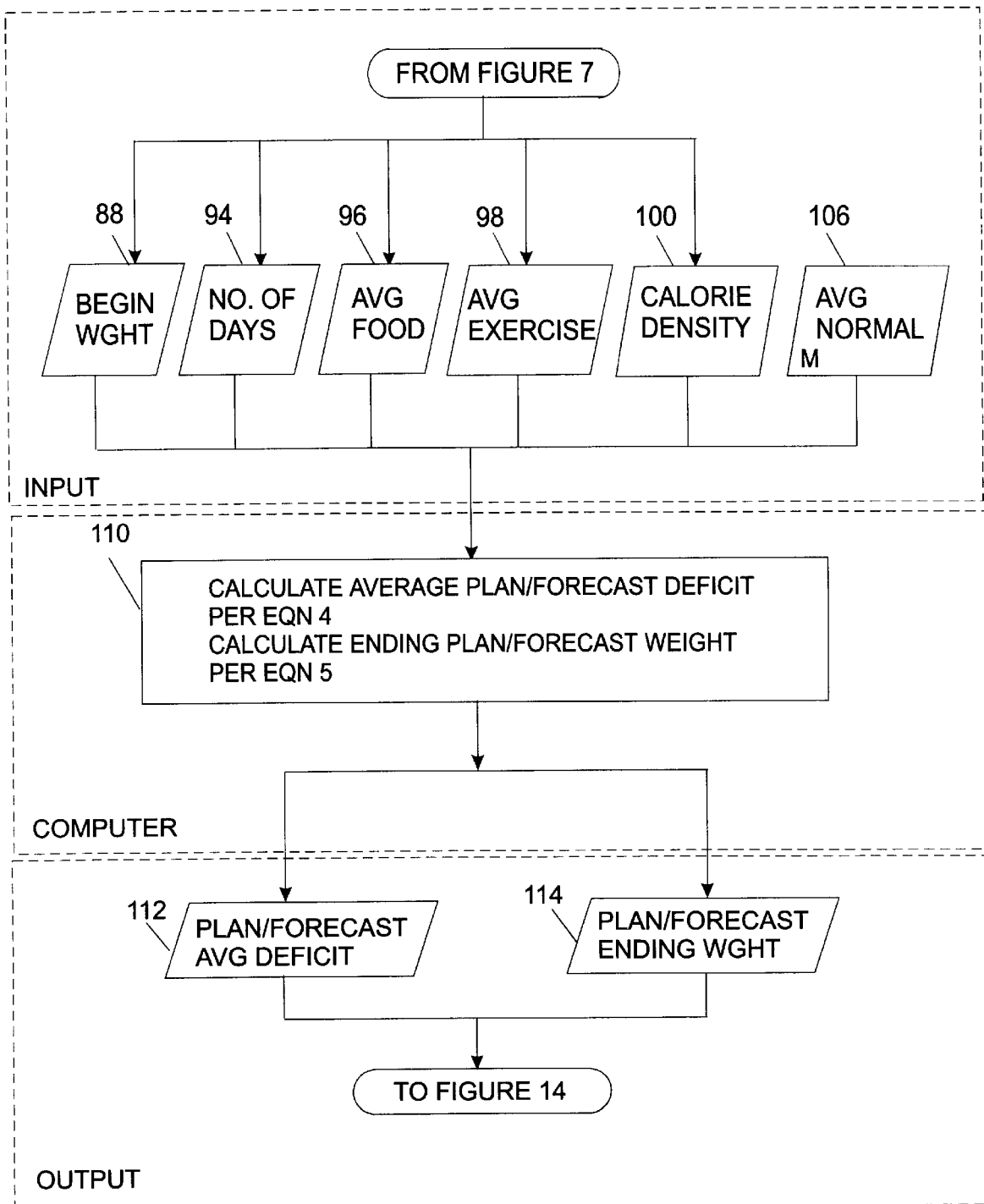
FIG. 8 is a detailed flow diagram showing how the system calculates the Plan/Forecast calorie deficit and ending weight.
Figure 10:
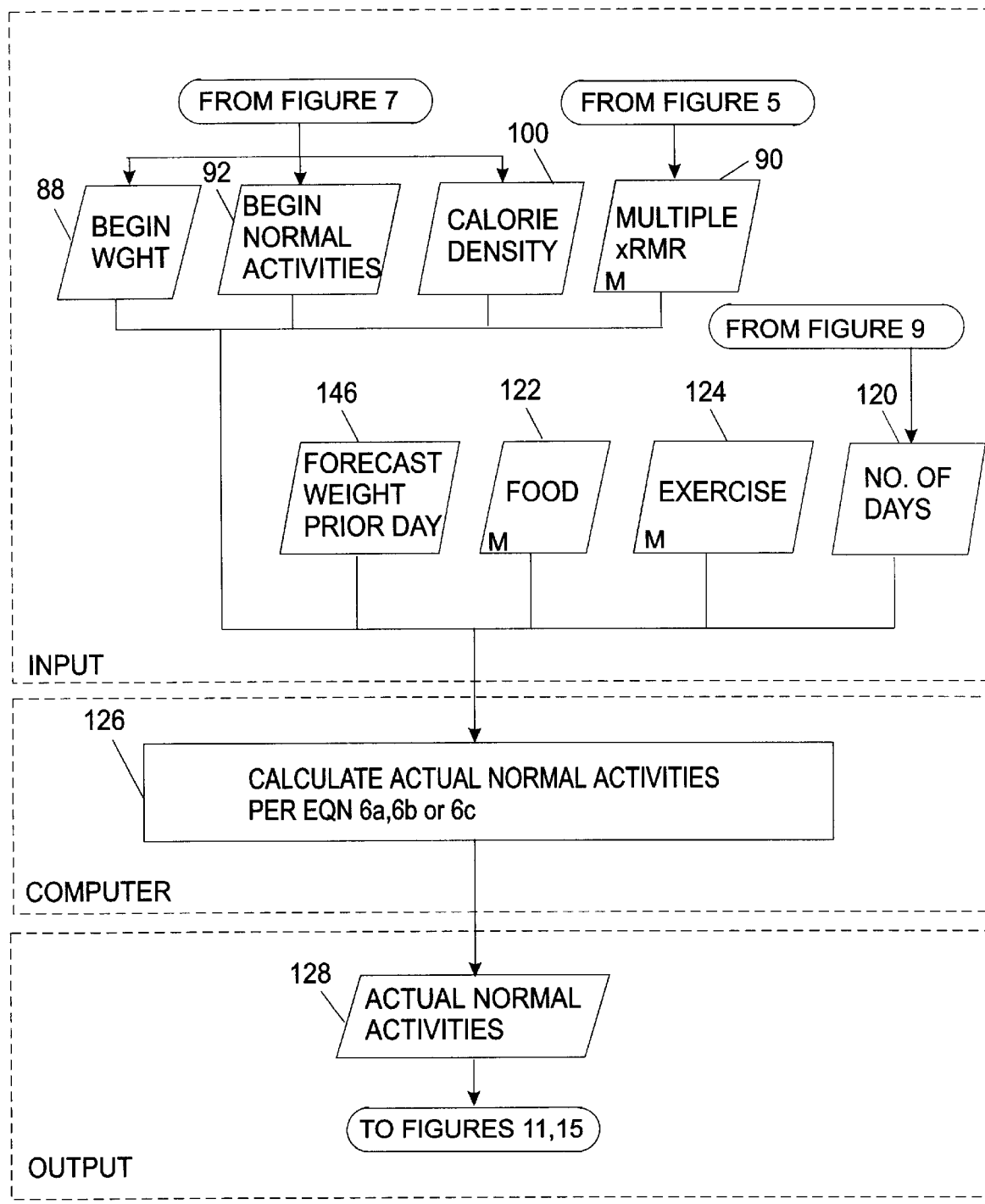
FIG. 10 is a detailed flow diagram showing how the system calculates the individual's actual daily normal activities calories.

Secondly, the individual constructs his or her weight loss Plan as seen in FIG. 7, FIG. 8 and FIG. 18. The individual enters his or her Beginning Actual Weight 88 in FIG. 7 and FIG. 18 and which is the same as 24 in FIG. 3 and FIG. 17. The individual also enters his or her Plan Initial Normal Activity Calories Multiple of Resting Metabolic Rate (xRMR) 90 as seen in FIG. 10 and FIG. 18 and which is the same as 66 in FIG. 5 and FIG. 17. The individual also enters his or her beginning Plan Initial Normal Activity Calories 92 as seen in FIG. 7 and FIG. 18 and which is the same as 68 in FIG. 5 and FIG. 17. Plan Initial Normal Activity Calories Multiple of Resting Metabolic Rate (xRMR) 90 and beginning Plan Initial Normal Activity Calories 92 as seen in FIG. 10, FIG. 7 and FIG. 18 is the same as Plan Initial Normal Activity Calories Multiple of Resting Metabolic Rate (xRMR) 66 and Plan Initial Normal Activity Calories 68 as seen in FIG. 5 and FIG. 17 since Plan Initial Normal Activity Calories Multiple of Resting Metabolic Rate (xRMR) 90 and beginning Plan Normal Activity Calories 92 are estimated at the same time the individual begins his or her weight loss program.

The individual also enters the Plan Number of Days 94 he or she plans to lose weight, Plan Average Food Calories 96 and Plan Average Exercise Calories 98 per day he or she is planning to achieve as seen in FIG. 7 and FIG. 18. The individual also enters his or her Plan Average Calorie Density 100 as seen in FIG. 7 and FIG. 18. Initially, Plan Average Calorie Density will be 3500 Cal/lb since no other calorie density information is available. Later, as the individual begins to accumulate information about his or her actual weight loss, the individual's Actual Average Calorie Density 184 of FIG. 16 and FIG. 18 will be estimated and can be used instead.

The final Plan input is Plan Average Normal Activity Calories 106 per day as seen in FIG. 8 and FIG. 18. Plan Average Normal Activity Calories 106 can be and usually is the same as the Calculated Plan Average Normal Activity Calories 108 which is based on all of the other Plan inputs as seen in FIG. 7 and FIG. 18.

Calculated Plan Average Normal Activity Calories 108 as seen in FIG. 7 and FIG. 18 represents the estimated average normal activities calories per day, the individual can expect to expend over the Plan Number of Days of the plan. Beginning Actual Weight 88, beginning Plan Initial Normal Activity Calories 92, Plan Number of Days 94, Plan Average Food Calories 96, Plan Average Exercise Calories 98 and Plan Average Calorie Density 100 are used as inputs for Calculated Plan Average Normal Activity Calories 108 as seen in FIG. 7. Since the individual is forecasting a weight decrease, Calculated Plan Average Normal Activity Calories 108 will be less than beginning Plan Initial Normal Activity Calories 92 because weight is forecasted to decrease.

Calculated Plan Average Normal Activity Calories 108 is computed as the ratio of Average Weight over the Plan or Forecast period to Beginning Actual Weight 88 multiplied by Plan Initial Normal Activity Calories 92 as defined and calculated in accordance with Equation 3a and Equation 3b.

$$(a)\ \overline{N}_{P/F,t} = \frac{\overline{W}_{P/F,t}}{W_o} N_o \tag{3}$$

where:

$\overline{N}_{P/F,t}$=Calculated Plan Average Normal Activity Calories 108 (Cal/day) over time period t,94

$\overline{W}_{P/F,t}$=Average Weight (lbs) over time period t,94

$W_0$=Beginning Actual Weight 88 (lbs) at time period t=0,94 and $N_0$=Plan Initial Normal Activity Calories 92 (Cal/day) at time period t=0,94 where:

$$(b)\ \overline{W}_{P/F,t} = W_o + \frac{F_{P/F,t} t}{2\rho_{P/F,t}} -$$

$$\frac{E_{P/F,t} t}{2\rho_{P/F,t}} - \frac{N_o}{k\rho_{P/F,t}} + \frac{1}{k}\ \frac{N_o}{(tk\rho_{P/F,t})}\ (1 - e^{-kt}) + Adj_{Plan/Act,1}$$

where:

$\overline{W}_{P/F,t}$=Average Weight (lbs) is substituted in Equation 3(a)

$W_0$=Beginningl Actual Weight 88 (lbs) at time period t=0,94

$\overline{F}_{P/F,t}$=Plan Average Food Calories 96 (Cal/day) over time period t,94

$\overline{E}_{P/F,t}$=Plan Average Exercise Calories 98 (Cal/day) over time period t,94

$N_0$=Plan Initial Normal Activity Calories 92 (Cal/day) at time period t=0,94

$\overline{\rho}_{P/F,t}$=Plan Average Calorie Density 100 (Cal/lb) over time period t,94

$$k = \frac{\left(\frac{N_o}{W_0}\right)}{\overline{\rho}_{P/F,t}}\ (1/day)$$

and:

$Adj_{Plan/Act,t}$,104, as seen in FIG. 7, is an adjustment so that Calculated Plan Average Normal Activity Calories 108 will be the same as Actual Average Normal Activity Calories 170 when the Plan data 94,96,98,100, is the same as the actual data 164,166,168,184

The inputs also permit the individual to see immediately, his or her Plan Average Calorie Deficit 112 which is computed as Plan Average Normal Activity Calories 106 plus Plan Average Exercise Calories 98 less Plan Average Food Calories 96. Plan Average Calorie Deficit 112 is seen in FIG. 8 and FIG. 18 is defined and calculated in accordance with Equation 4.

$$\overline{Deficit}_{P/F,t} = [\overline{N}_{P/F,t} + \overline{E}_{P/F,t} - \overline{F}_{P/F,t}] \tag{4}$$

where:

$\overline{Deficit}_{P/F,t}$=Plan Average Calorie Deficit 112 (Cal/day) over time t,94

$\overline{N}_{P/F,t}$=Plan Average Normal Activities Calories 106 (Cal/day) over time t,94

$\overline{E}_{P/F,t}$=Plan Average Exercise Calories 98 (Cal/day) over time t,94

$\overline{F}_{P/F,t}$=Plan Average Food Calories 96 (Cal/day) over time t,94 and where deficits are defined to be postive

The individual's Plan Ending Plan Weight 114 is also calculated by Equation 5 and is seen in FIG. 8 and FIG. 18 is defined and calculated in accordance with Equation 5.

$$W_{P/F,t} = W_o - \left(\frac{\overline{Deficit}_{P/F,t}}{\overline{\rho}_{P/F,t}}\right) t \tag{5}$$

where:

where:

$W_{P/F,t}$=Plan or Forecasted Ending Weight 114 (lbs) at time period t,94

$W_0$=Beginning Actual Weight 88 (lbs) at time period t=0,94

($\overline{Deficit}_{P/F,t}$)

=Plan Average Calorie Deficit 112 (Cal/day) over time period t,94

$\overline{\rho}_{P/F,t}$=Plan Average Calorie Density 100 (Cal/lb) over time period t,94

For example, as seen in FIG. 18, the individual entered Beginning Actual Weight 88 of 182.0 lbs, Plan Initial Normal Activity Calories Multiple of Resting Metabolic Rate (xRMR) 90 of 1.5, beginning Plan Initial Normal Activity Calories 92 of 2681 Cal/day, Plan Number of Days 94 as 30 days, Plan Average Food Calories 96 of 2000 Cal/day, Plan Average Exercise Calories 98 of 400 Cal/day and Plan Average Calorie Density 100 of 2935 Cal/lb. Calculated Plan Average Normal Activity Calories 108 was computed to be 2619 Cal/day which the individual manually entered into Plan Average Normal Activity Calories 106. The computer calculated the Plan Average Calorie Deficit 112 as (2619+400−2000)=1019 Cal/day. Plan Ending Weight 114 is computed as 182.0−(1019/2935)×30=171.6 lbs.

Recording, Reporting and Understanding the Weight Loss Process

Figure 9:
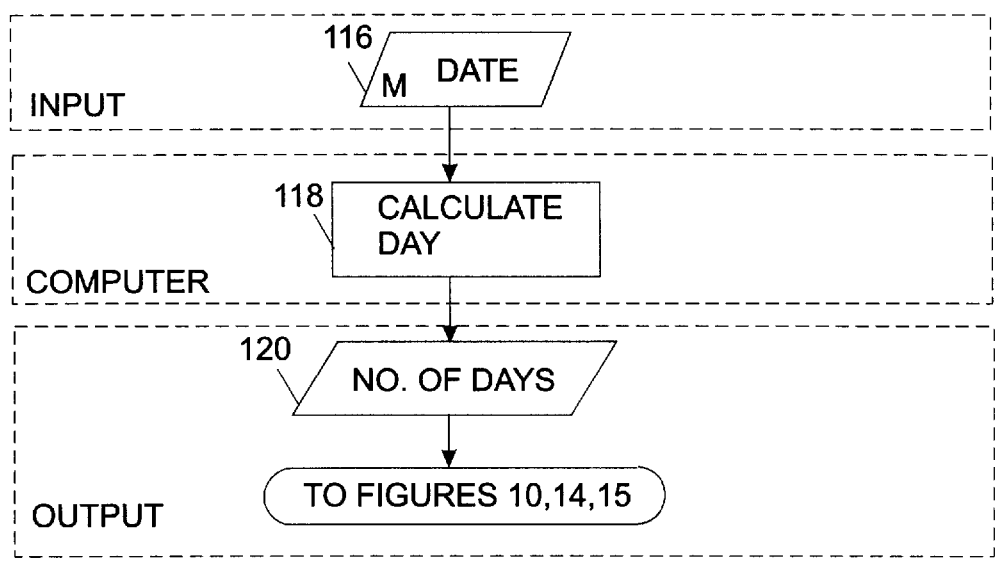
FIG. 9 is a detailed flow diagram showing how the system calculates the number of days on the Plan based on the date.

Thirdly, the individual begins executing his or her weight loss plan. The individual must record the day's Actual Date 116, and daily estimates of his or her Actual Food Calories 122 and Actual Exercise Calories 124 as seen in FIG. 9, FIG. 10 and FIG. 18. Actual Days of Plan 120 are calculated from the entered Actual Date 116 and is seen in FIG. 9 and FIG. 18. All Dates 116 and Days 120 are consecutive and cannot be skipped. Actual Food Calories 122 are the estimated calories the individual consumes each day. Actual Exercise Calories 124 are the gross or total calories the individual expends on exercise each day. These are exogenous inputs coming from food labels, food calorie tables, fitness machines or other sources. These estimates are not intended nor can they be exact. Rather, they represent honest best estimates.

Figure 13:
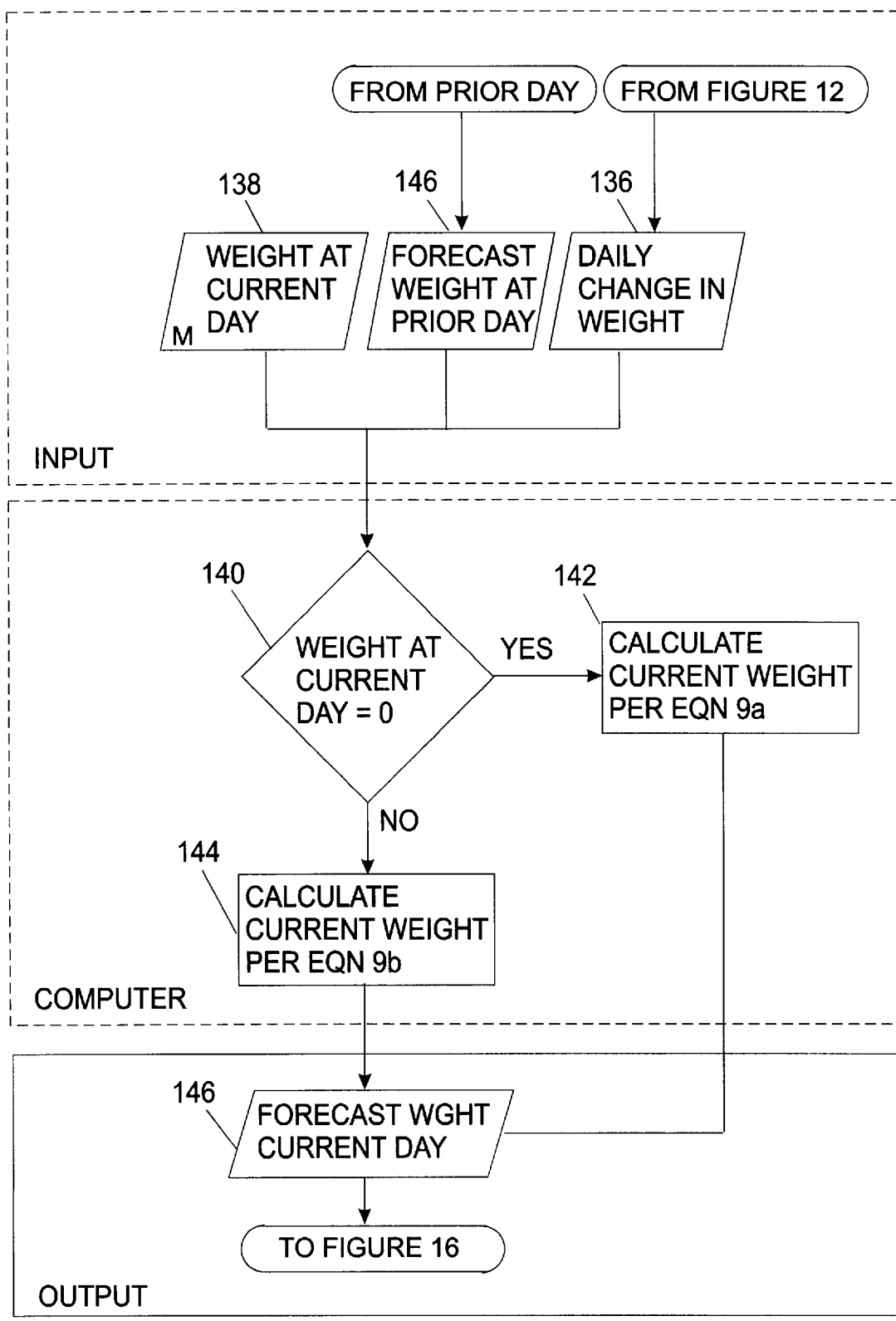
FIG. 13 is a detailed flow diagram showing how the system calculates the individual's forecasted ending weight.

The individual also enters his or her Actual Weight 138 as seen in FIG. 13 and FIG. 18 whenever he or she weighs himself or herself. More frequent weighings produce more accurate results in a shorter time period. The individual can select whether he or she weighs himself or herself at the beginning or end of the day. The algorithms are adjusted by conventional means to include or exclude the current day's calories from the current day's forecasted ending weight.

Figure 11:
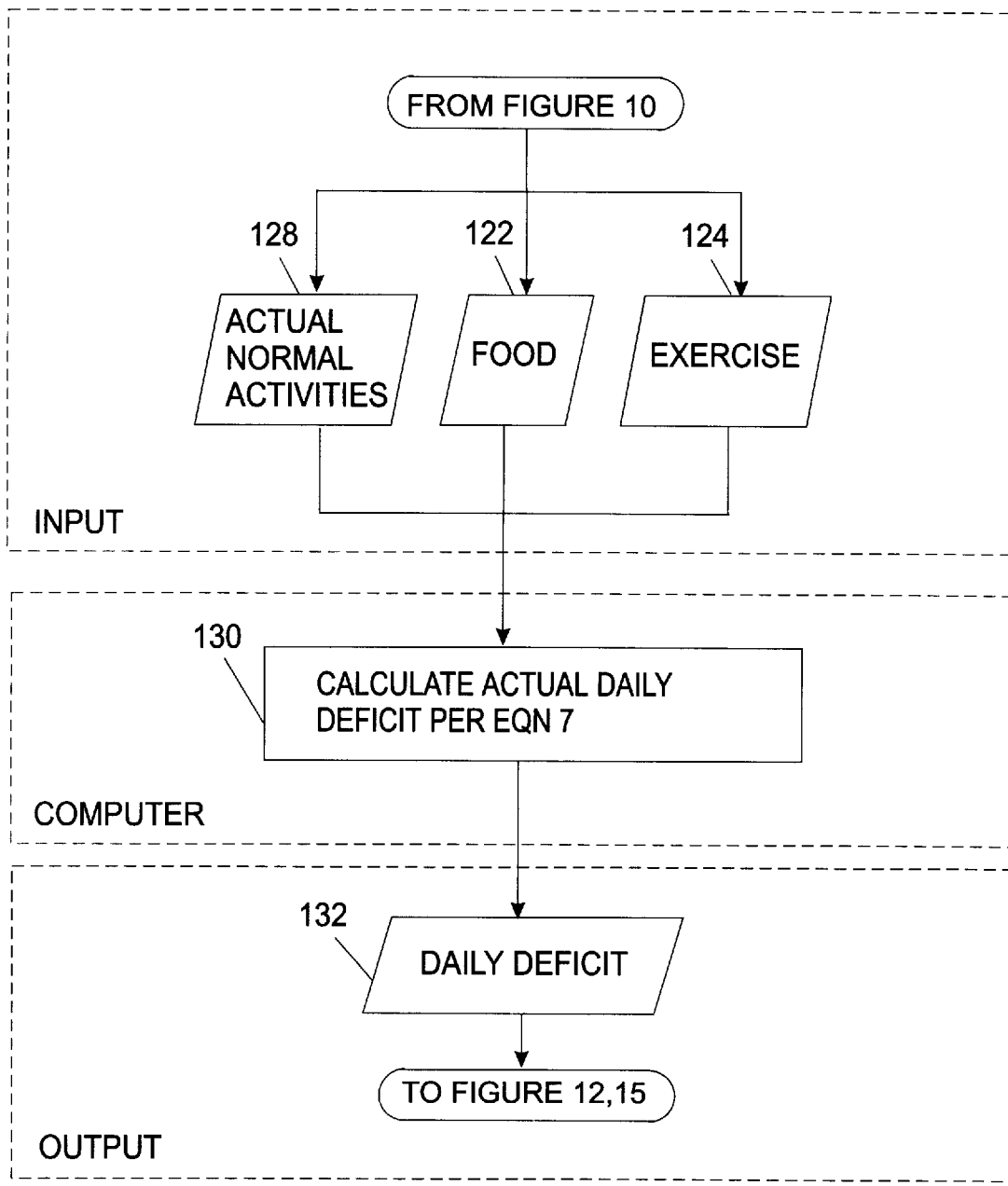
FIG. 11 is a detailed flow diagram showing how the system calculates the individual's daily calorie deficit.

The computer also automatically estimates the individual's daily Actual Normal Activities Calories 128 which is seen in FIG. 10 and FIG. 18 and is included as part of the daily Actual Calorie Deficit 132 of FIG. 11 and FIG. 18. The individual's daily Actual Normal Activity Calories 128 is based on the following relationship as shown in Equation 6a, 6b and 6c.

$$(a)\ N_{A,t} = \left[ \left( \frac{N_o}{xRMR} \right) + 6.25\Sigma(\Delta W_{A,t-1}) \right] xRMR \text{ for Males} \tag{6}$$

$$(b)\ N_{A,t} = \left[ \left( \frac{N_o}{xRMR} \right) + 4.35\Sigma(\Delta W_{A,t-1}) \right] xRMR \text{ for Females}$$

$$(c)\ N_{A,t} = \left[ \left( \frac{N_o}{xRMR} \right) + 5.30\Sigma(\Delta W_{A,t-1}) \right] xRMR \text{ for Males or Females}$$

where:
$N_{A,t}$=Actual Normal Activity Calories (Cal/day) at time period t,120
$N_o$=Plan Initial Normal Activity Calories 92 (Cal/day) at time period t=0,120
xRMR=Plan Initial Normal Activity Calories Multiple of Resting Metabolic Rate (xRMR) 90 at time period t,=0 120
$\Delta W_{A,t-1}$=Change in Actual Forecast Weight 136 (lbs) at time period t−1,120
where 6.25, 4.35 and 5.30 are the average rates of change of resting metabolism per lb-day from Equation (2a) and (2b) converted to the English system and where 5.30 is the average of 6.25 and 4.35 and can be used instead without loss of accuracy as seen in and used in FIG. 18

This relationships says that the individual's Actual Normal Activity Calories 128 on any day is equal to the individual's initial resting metabolism adjusted by 6.25 or 4.35 or 5.30 calories per pound of cumulative weight change from initial weight and converted to the individual's normal activities by multiplying by the individual's multiple of his resting metabolic rate. Weight decreases cause resting metabolism to decrease and normal activity calories to decrease. Conversely, weight increases cause resting metabolism to increase and normal activity calories to increase. The Actual Normal Activity Calories estimate shown in Equation (6a) and Equation (6b) and Equation (6c) is mathematically consistent with the beginning Plan Initial Normal Activity Calories 92 and Plan Initial Normal Activity Calories Multiple of Resting Metabolic Rate (xRMR) 90 as all are derived from the same equations (2a) and (2b) causing no calorie imbalances.

For example, at Day 3 as used in FIG. 18, Actual Normal Activity Calories 128 is [(2681/1.5)+5.30×(181.0−182)]×1.50=2673 Cal/day.

The individual's daily Actual Calorie Deficit 132 as seen in FIG. 11 and FIG. 18 is defined and calculated in accordance with Equation 7.

$$\text{Deficit}_{A,t}=[N_{A,t}+E_{A,t}-F_{A,t}] \tag{7}$$

where:
Deficit$_{A,t}$=Actual Calorie Deficit 132 (Cal/day) at time t,120
$N_{A,t}$=Actual Normal Activity Calories (Cal/day) at time t,120, from equation (6)
$E_{A,t}$=Actual Exercise Calories 124 (Cal/day) at time t,120
$F_{A,t}$=Actual Food Calories 122 (Cal/day) at time t,120
and where weight loss deficits are defined to be postive For example, at Day 3 as seen in FIG. 18, the daily Actual Calorie Deficit 132 is (2673+0−2200)=473 Cal/day.

Figure 12:
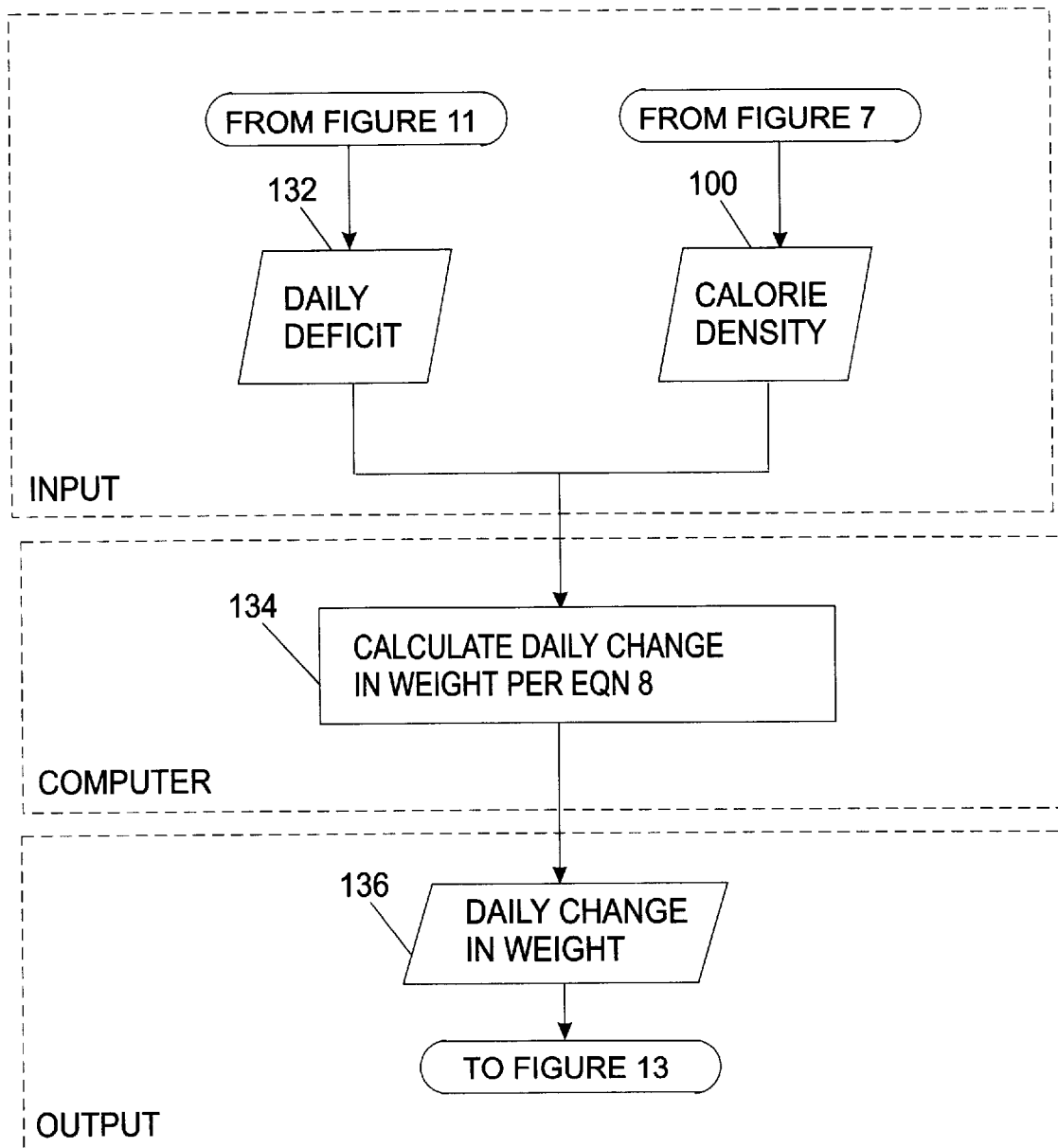
FIG. 12 is a detailed flow diagram showing how the system calculates the individual's change in daily weight.

Daily Actual Forecast Weight Change 136 as seen in FIG. 12 and FIG. 18 is defined and calculated in accordance with Equation 8.

$$\text{Daily Change}_{A,t} = - \left[ \frac{\text{Deficit}_{A,t}}{\bar{\rho}_{P/F,t}} \right] \tag{8}$$

where:
Daily Change$_{A,t}$=Actual Forecast Weight Change 136 (lbs/day) at time period t,120
Deficit$_{A,t}$=Actual Calorie Deficit 132 (Cal/day) at time period t,120
$\bar{\rho}_{P/F,t}$=Plan/Forecast Average Calorie Density 100 (Cal/lb) at time period t,120

Note: Actual daily weight change 136 uses $\bar{\rho}_{P/F,t}$100. The individual can replace the current value of $\bar{\rho}_{P/F,t}$100 with $\bar{\rho}_{A,t}$184 thereby integrating the Plan and Actual for the latest calorie density providing greater accuracy and consistency For example, at Day 3 as seen in FIG. 18, the daily Actual Forecast Weight Change 136 is—473/2935=−0.16 lbs.

Daily Actual Forecast Weight 146 as seen in FIG. 13 and FIG. 18 is defined and calculated in accordance with Equation 9.

$$W_t=W_{t-1}+\text{Daily Change}_{A,t} \text{ if } W_{A,t}=0 \tag{9}(a)$$
$$W_t=W_{A,t}+\text{Daily Change}_{A,t} \text{ if } W_{A,t}>0 \tag{9}(b)$$

where:
$W_t$=Actual Forecast Weight 146 (lbs) at time period t,120
$W_{t-1}$=Actual Forecast Weight 146 (lbs) at prior time period t−1,120
$W_{A,t}$=Actual Forecast Weight 138 (lbs) at time period t,120

Daily Change$_{A,t}$=Actual Forecast Weight Change 136 (lbs) at time t,120

For example at Day 3 as seen in FIG. 18, the Actual Forecast Weight 146 is 181.0−0.16=180.8 lbs. If the individual had weighed himself or herself at the beginning of Day 4 and weighed 179.0 lbs as seen in FIG. 18, Actual Forecast Weight 146 is 179.0−0.40=178.6 lbs.

Figure 14:
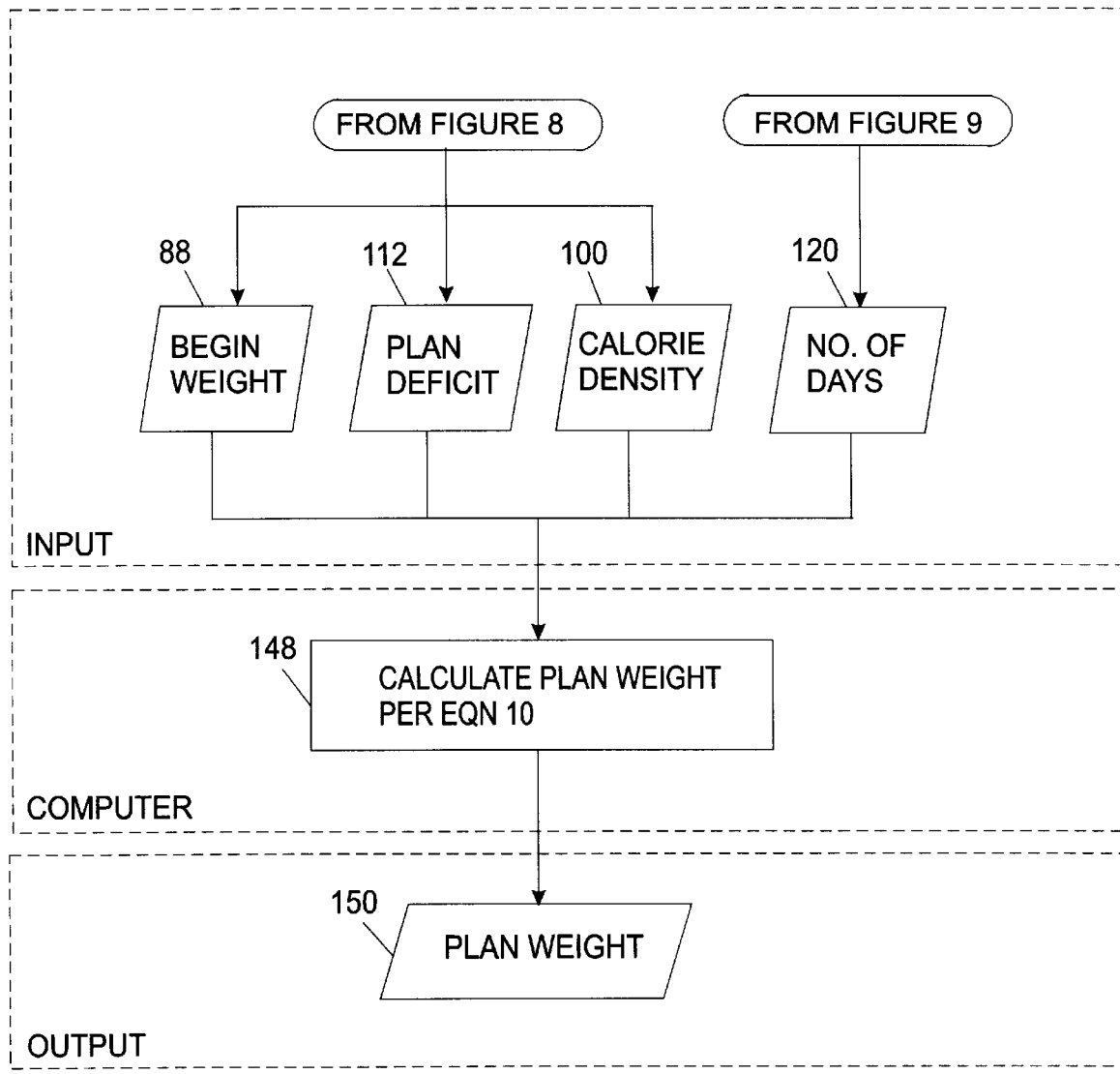
FIG. 14 is a detailed flow diagram showing how the system calculates and synchronizes the individual's weight Plan with current forecasted weight for the same period.

Plan Weight 150 as seen in FIG. 14 and FIG. 18 is defined and calculated in accordance with Equation 10.

$$W_{Plan,t} = W_o - \frac{\text{Deficit}_{P/F,t}T}{\bar{\rho}_{P/F,t}} \qquad (10)$$

$W_{Plan,t}$=Plan Weight 150 (lbs) at time period t,120

$W_0$=Beginning Actual Weight 88 (lbs) at time period t=0,120

Deficit$_{P/F,t}$=Plan/Forecast Deficit 112 (Cal/day) at time period t,120

$\bar{\rho}_{P/F,t}$=Plan/Forecast Average Calorie Density 100 (Cal/lb) at time period t,120

T=Actual Days of Plan 120 (Days) at time period t=T

For example, at Day 3 as seen in FIG. 18, the Plan Weight 150 is 182.0−(1019/2945)×3=181.0 lbs.

Figure 15:
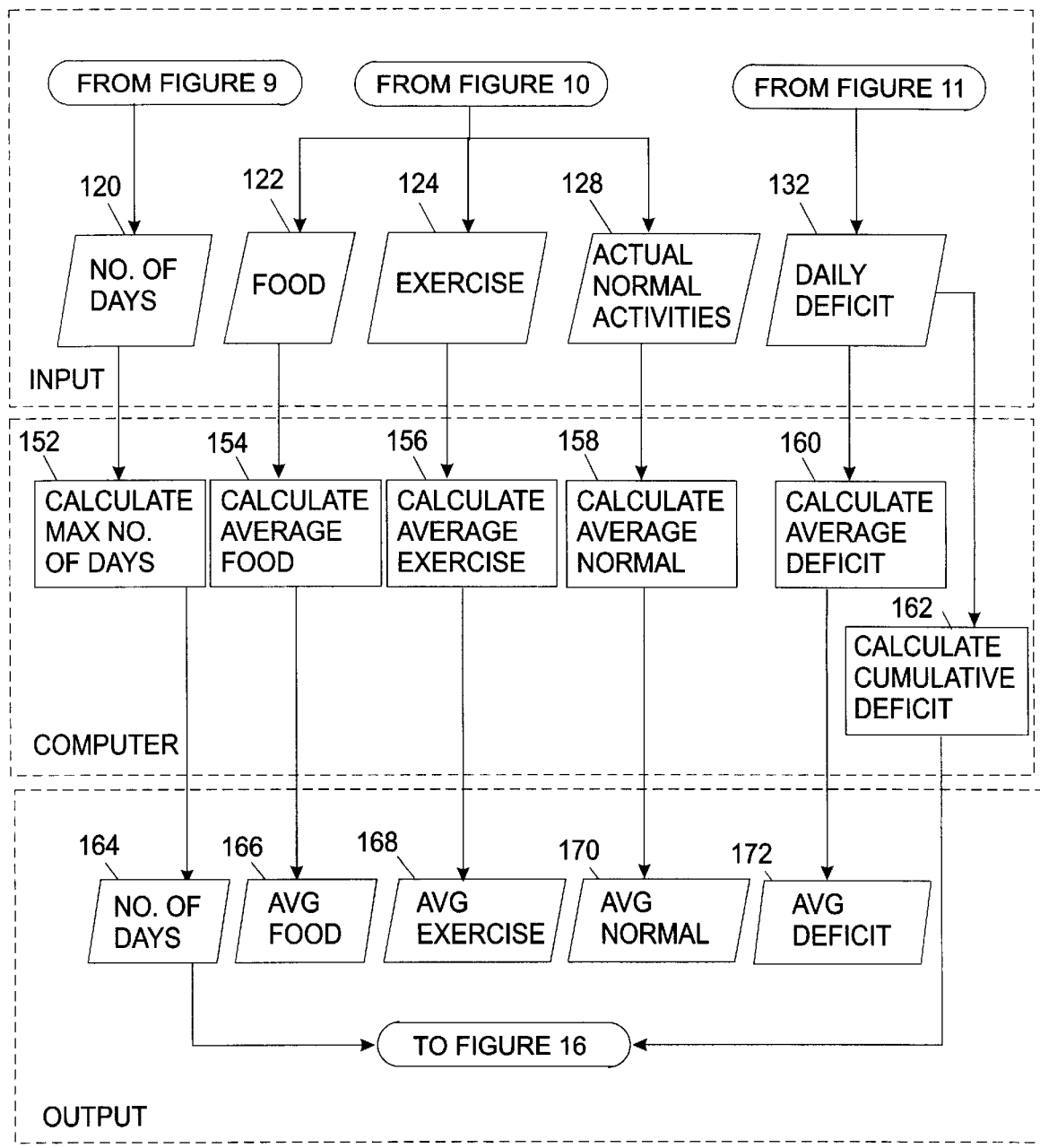
FIG. 15 is a detailed flow diagram showing how the actual data from the database rolls-up to summary statistics.
Figure 16:
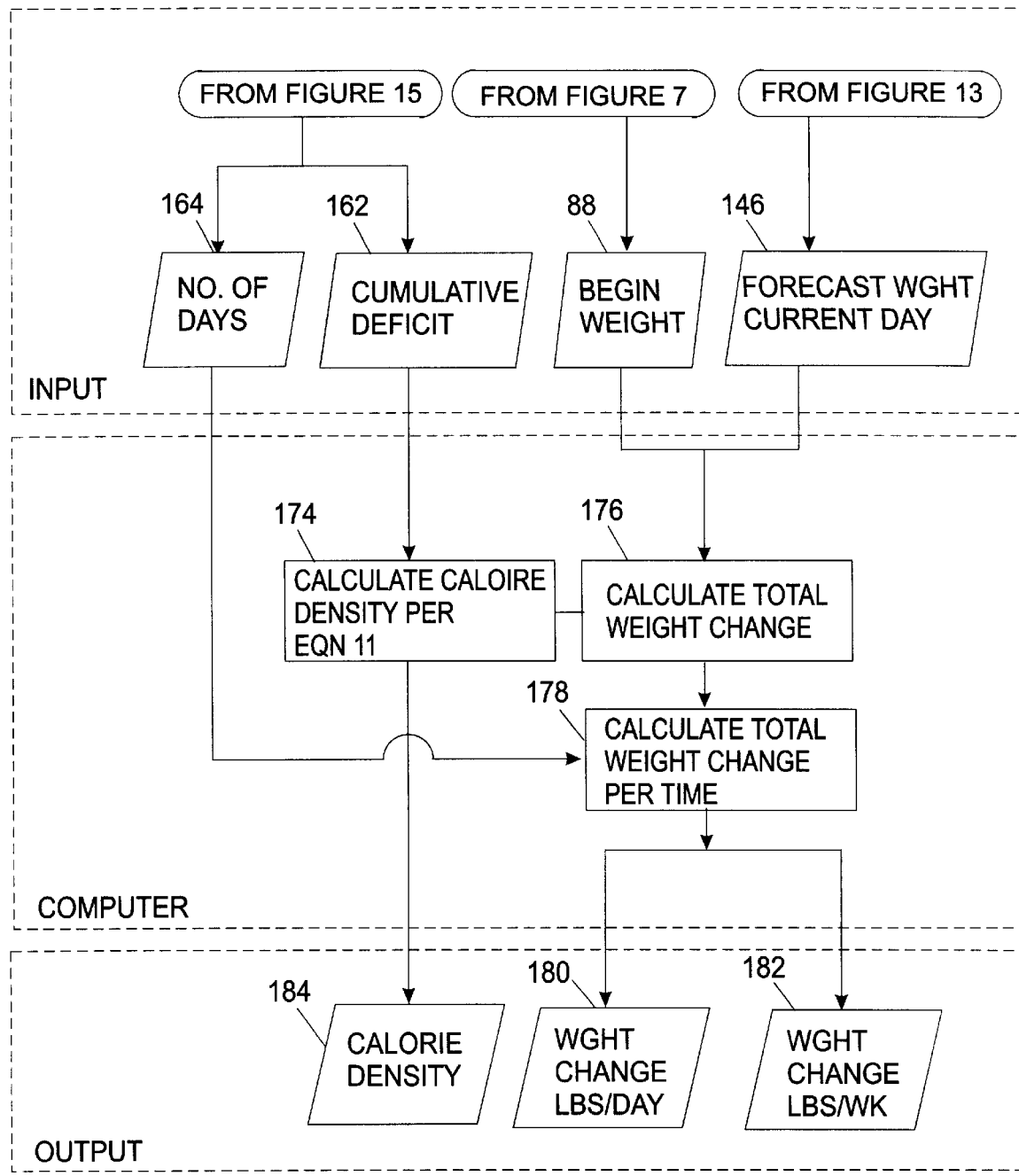
FIG. 16 is a detailed flow diagram showing how the actual data from the database is summarized to compute change in weight and individual calorie density.

All of the individual's data in the database is averaged and summarized. The Actual Days of Plan 164, as well as the individual's daily Actual Average Food Calories 166, daily Actual Average Exercise Calories 168, daily Actual Average Normal Calories 170 and daily Actual Average Deficit Calories 172 are computed per conventional means as seen in FIG. 15 and FIG. 18. The individual's average Weight Change in lbs/day 180 and lbs/week 182 and Actual Average Calorie Density 184 are computed as seen in FIG. 16 and FIG. 18. Averages for Weight Changes 180,182 and Actual Average Calorie Density 184 are calculated per conventional arithmetic averaging techniques.

Actual Average Calorie Density 184 is defined as the Cumulative Actual Calorie deficit 162 divided by the Cumulative Actual Forecast Weight Change 176 as seen in FIG. 15 and FIG. 16 and defined by Equation 11.

$$\bar{\rho}_{A,t} = \frac{\Sigma \text{Deficit}_{A,t}}{\Sigma \Delta W_{A,t}} \qquad (11)$$

where:

$\bar{\rho}_{A,t}$=Actual Average Calorie Density 184 (Cal/lb) over time period t,120

$\Sigma$Deficit$_{A,t}$=Cumulative Actual Calorie Deficit 132 (Cal) over time period t,120

$\Sigma\Delta W_{A,t}$=Cumulative Actual Forecast Weight Change 146 (lbs) over time period t,120 where deficits and decreases in weight are defined to be postive

For example, at Day 9 as seen in FIG. 18, Actual Average Calorie Density 184 is (12457)/(182.0−177.4)=2711 Cal/lb.

An individual's calorie density is particular to the individual's system for calorie counting and his body's reaction to a calorie deficit. Typically, calorie density is low during the first few weeks of weight loss due to excess water loss. Thereafter, it increases and will vary over time.

Actual Average Calorie Density 184 is used to control the individual's weight loss process. In the most common case, an individual will systematically consume more food calories than reported. This will result in less weight decrease decreasing the denominator of Equation 11 and causing a rise in the individual's calorie density of Equation 11.

If all of the individual's calorie estimates and weights were perfect, calorie density should average about 3500 Cal/lb. However, since an individual's calories estimates are not perfect, the larger the individual's calorie density deviates from 3500 Cal/lb the less accurate are the calorie estimates. An upper limit of about more than about 6000 Cal/lb suggests that the individual's calorie counting is getting too loose at about the 95% confidence limits (absent excessive body water shifts, weight plateauing or slowing resting metabolic rate).

Due to unknown errors in the actual calorie estimates, the individual's absolute calorie density can never be known with certainty. However, by defining calorie density to be cumulative over time, random calorie errors will tend to cancel each other out resulting in a more accurate absolute estimate of calorie density.

If the individual replaces his or her Plan Average Food Calories 96 with his or her Actual Average Food Calories 166, and replaces his or her Plan Average Exercise Calories 98 with his or her Actual Average Exercise Calories 168, and replaces his or her Plan Average Normal Activity Calories 106 with his or her Actual Average Normal Activity Calories 170, and replaces his or her Plan Average Calorie Density 100 with his or her Actual Average Calorie Density 184 as seen in FIG. 18, Plan Ending Weight 114 as seen in FIG. 8 and FIG. 18 will be accurate. This is because systematic errors contained within the actual calories 166,168,170 and actual calorie densities 184, are the same and are eliminated.

There are expected to be several likely errors in the data which sets a maximum number of food calories the individual should consume in order to insure that he or she will actually begin to lose weight. The expected range of errors in beginning Plan Initial Normal Activity Calories 92 is a minimum of about ±0% to ±25% or more. The expected range of errors in Plan Average Exercise Calories 98 is about ±0% to ±25% or more. It is possible that the individual's "true" normal activities calories and exercise calories can be consistently lower than estimated. To adjust Plan Average Food Calories 96 for this possibility, the individual should add both his or her beginning Plan Initial Normal Activity Calories 92 and Plan Average Exercise Calories 98 together and multiply by 0.75. The result would be the maximum number of Plan Average Food Calories 96 the individual should Plan on eating to be 95% confident that he or she would begin to lose weight.

The format shown in FIG. 18 is not limiting and can display in many other different formats.

Other Advantages of Controlling Weight Loss

Figure 1:
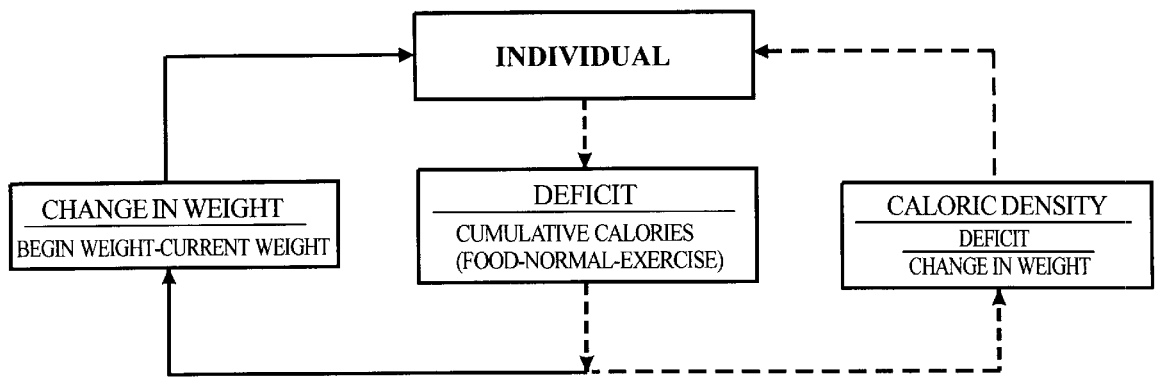
FIG. 1 is seen to describe the way an individual loses weight. The individual firstly, creates a calorie deficit and secondly, the individual's body reacts by decreasing it's weight.
Figure 2:
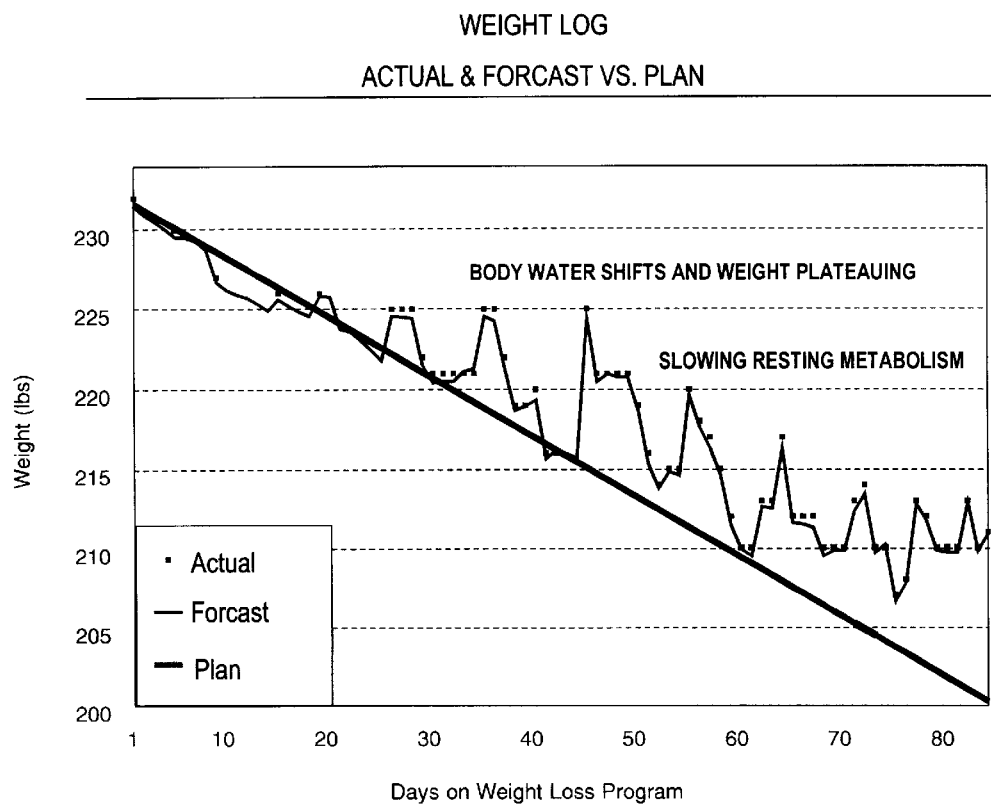
FIG. 2 shows one embodiment of a graphical display of the same individual's weight loss data, contained within said database, showing Actual Weight, Forecast Weight and Plan Weight and body water shifts, weight plateauing and possible slowing resting metabolic rate changes.

The individual maintains control by seeing the differences between what he or she is planning to do and what he or she is actually doing as seen in FIG. 2 and FIG. 18. The Plan variables and the Actual results are defined to be exactly the same. By analyzing the biggest differences between Plan and Actual variables, the individual can readily determine the reasons for the variances, thereby enabling him or her to take corrective action.

By knowing the numbers, the individual can experiment with what is comfortable for him or her, trying out various food and/or exercise scenarios. Once a comfortable scenario is established, he or she can set the Plan numbers that he or she can live with and still be committed to accomplishing the resulting goals. In this way the individual can lose weight comfortably without undue effort and stress and with commitment and desire.

The individual can experiment with many "what-if" scenarios to optimize the weight loss plan for his or her own goals and time constraints. If his or her goals change, changing the Plan is easy and the expected results seen.

Since weight loss is a cumulative effect, the individual need not adhere to a constant level of calorie deficits each day. If he or she wants to hit his or her goals by the end of the Plan period, he or she can do so flexibly, by incurring varying caloric deficits yet which cumulatively can be on Plan over the Plan's time period.

Oftentimes, the individual may want to see what his or her efforts to-date imply about the future, all other factors being the same. As seen in FIG. 18, the individual can do this simply by entering his or her reported Actual Day of Plan 164 into 94, Actual Average Food Calories 166 into 96, Actual Average Exercise Calories 168 into 98, and Actual Average Normal Activity Calories 170 into 106 and Actual Average Calorie Density 184 into 100. Calculated Plan Average Normal Activity Calories 108 will then be the same as Plan Average Normal Activity Calories 106 and Actual Average Normal Activity Calories 170. By varying the Plan Number of Days 94, and adjusting Plan Average Normal Activity Calories 106 to be the same as Calculated Plan Average Normal Activity Calories 108, the individual can forecast what he or she can expect in terms of future Plan Ending Weight 114, all other factors remaining constant.

Viewing the Data in Graphical Form

The relevant data is further presented to the individual in graphical form. As seen in FIG. 2, this graph shows Weight on the Y-Axis and shows the Actual Days of the Plan 120 on the X axis. It further shows the individual's Actual Weight 138, Forecast Actual Weight 146 and Plan Weight 150.

The individual's Actual Weight 138 is the weight seen on the weight scales. Actual weight may not be "true" weight due to excess body water but is the best empirical measure of an individual's weight.

The individual's Forecast Actual Weight 146 is what the individual would weigh calculated from his or her cumulative daily calorie deficit from the individual's last weighing. In the absence of actual weight, it is the "true" weight of the individual.

The individual's Plan Weight 150 is the weight the individual ought to weigh consistent with his or her Plan at the same point in time. It reflects average goals for the current time period. It disregards body water shifts and weight plateauing and assumes the individual's resting metabolic rate does not change except due to normal body weight changes.

By presenting the data this way, the individual can see at a glance, how he or she is doing compared to Plan. He or she can also see quite clearly, weight changes due to water body shifts, weight plateauing and weight changes due to major shifts in resting metabolism.

Many individuals do not lose weight in a straight line. Goals change, daily food and or exercise calories are not always the same. Daily actual weight can decrease, remain the same or increase obscuring the fact that the individual is actually losing weight. By plotting the data this way, the individual can see his or her weight trends while still being motivated to continue.

Some people on a weight loss program may experience a change in their resting metabolic rate. Studies show that an individual's resting metabolic rate may change and it may speed up, remain the same or slow down in response to a diet and/or exercise program. The graph visually shows the individual if his or her resting metabolic rate is fundamentally changing. It may show up as a slow systematic secular increase in the individual's weight against the Plan as seen in FIG. 2.

It is also possible that the individual's weight loss will be significantly faster or slower than Plan.

If this happens, the individual can adjust his or her Plan, by varying the Plan inputs, to graphically overlay, and align the Plan to the individual's actual weight loss experience. By so doing, the individual produces one solution (out of many) of all of the variables causing the individual's weight loss thereby suggesting other reasons for weight loss.

The graphical solution highlights both body water shifts, weight plateauing and major resting metabolism changes and uncovers and redirects the individual to yet another and different set of issues. Effective solutions to body water, weight plateauing and resting metabolism are quite different as body water is typically temporary and can be controlled while resting metabolism changes cannot.

Body water shifts are random oscillations and will usually dissipate themselves over a few days.

Weight plateauing caused by dietary water retention (usually due to excess sodium) may remain for several weeks or more. Weight plateauing is characterized by abrupt weight increases or decreases with no weight changes for several days to several weeks. If the individual seeks to accelerate the dissipation of retained body water naturally and more quickly, say, seeking short term reassurance that the displayed body water is real, he or she can cut back on his or her food calories even more, switch to foods high in fat and/or protein, consume more water, or shift to a diet higher in potassium. These actions either singularly or in combination will usually eliminate dietary body water within a few days.

If the individual's resting metabolism begins to slow down, however, the individual has far fewer options. If the slowdown is not onerous, the individual can continue but at a lower rate of weight loss. The individual can also increase his or her caloric deficit even more to maintain his or her current weight loss. However, if the rate of slowdown is excessive and weight loss really slows down, the individual is wise to terminate his or her program. Usually, after resuming a normal eating pattern, the individual's resting metabolic rate will return to normal within about 3 to 4 weeks. At that time the individual can resume where he or she left off, having a complete report to begin anew.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A method for reducing or increasing an individual's actual weight, the method comprising the steps of:

a) planning a daily Calories Expended, and a daily Calories Intake, for calculating a Plan Calorie Deficit and a Plan Ending Weight;

b) recording an Actual Date, an Actual Food Calories and an Actual Exercise Calories into a database daily;

c) calculating an Actual Normal Activity Calories from steps (a) and (b) daily;

d) calculating an Actual Calorie Deficit from steps (b) and (c) daily;

e) calculating an Actual Forecast Weight Change from steps (a), (b) and (d) daily;

f) calculating an Actual Forecast Weight from steps (b) and (e) daily;

g) calculating the daily Plan Weight from steps (a) and (b) daily;

h) calculating an Actual Average Food Calories from the daily Actual Food Calories, an Actual Average Exercise Calories from the daily Actual Exercise Calories, an Actual Average Normal Activity Calories from the daily Actual Normal Activity Calories, an Actual Average Calorie Deficit from the daily Actual Calorie Deficit and the Cumulative Actual Forecast Weight Change from the daily Actual Forecast Weight Change from steps (b), (c), (e) and (f);

i) calculating an Actual Average Calorie Density from step (h);

j) calculating the Plan Calorie Deficit and Plan Ending Weight;

k) adjusting eating and exercising habits to move toward and achieve the Plan Calorie Deficit;

l) repeating steps (b) through (k) daily until Plan Ending Weight is reached.

2. The method of claim 1 wherein step (a) comprises the further step of calculating an Initial Plan Normal Activity Calories comprising the steps of:

a') recording the individual's Sex, Age, Beginning Actual Weight, Height, Number of Weekday Days per Week, Number of Weekend Days per Week, a Description of Weekday Activities, a Description of Weekend Activities, an Activity Coefficient Multiple (xRMR) for each activity, a Weekday Hours spent and a Weekend Hours spent on each activity;

b') calculating a Plan Resting Metabolic Rate as follows:

$$\text{Male } RMR = 66.47 + 13.75W + 5H - 6.755A \quad (a)$$

$$\text{Female } RMR = 655.1 + 9.56W + 1.85H - 4.68A \quad (b)$$

where:
RMR=Plan Resting Metabolic Rate (Cal/day)
W=Nude Beginning Actual Weight (kg) where $45 \leq W \leq 136$ kg
H=Barefoot Height (cm) where $152 \leq H \leq 213$ cm c') calculating a weighted average Plan Initial Normal Activity Calories from step (a');

d') Calculating a Plan Initial Normal Activity Calories Multiple of Resting Metabolic Rate (x RMR) by dividing the Plan Initial Normal Activity Calories by the Plan Resting Metabolic Rate of step (b') and (c');

e') measuring an Actual Resting Metabolic Rate; and f') calculating a more accurate Plan Initial Normal Activity Calories using the Actual Resting Metabolic Rate of step (e');

g') calculating a more accurate Plan Initial Normal Activity Calories Multiple of Resting Metabolic Rate (xRMR) by dividing the Plan Initial Normal Activity Calories by the Actual Resting Metabolic Rate of step (e').

3. The method of claim 1 wherein Step (a) comprises the further step of calculating individual's Calculated Plan Average Normal Activity Calories and entering the individual's Beginning Actual Weight, Plan Initial Normal Activity Calories, Plan Number of Days, Plan Average Food Calories, Plan Average Exercise Calories and Plan Average Calorie Density; the Calculated Plan Average Normal Activity Calories being calculated according to:

$$(a)\ \overline{N}_{P,t} = \frac{\overline{W}_{P,t}}{W_o} N_o$$

where:

$\overline{N}_{P,t}$=Calculated Plan Average Normal Activity Calories (Cal/day) over time period t $\overline{W}_{P,t}$=Average Weight (lbs) over time period t $W_0$=Beginning Actual Weight (lbs) at time period t=0 and $N_0$=Plan Initial Normal Activity Calories (Cal/day) at time period t=0 where:

$$(b)\ \overline{W}_{P,t} = W_o + \frac{\overline{F}_{P,t}}{2\overline{\rho}_{P,t}} - \frac{\overline{E}_{P,t}}{2\overline{\rho}_{P,t}} - \frac{N_o}{k\overline{\rho}_{P,t}} + \frac{1}{k} \frac{N_o}{(tk\overline{\rho}_{P,t})}(1 - e^{-kt} + Adj_{Plan/Act,t})$$

where:

$\overline{W}_{P,t}$=Average Weight (lbs) is substituted in Equation (a)

$W_0$=Beginning Actual Weight (lbs) at time period t=0

$\overline{F}_{P,t}$=Plan Average Food Calories (Cal/day) over time period t $\overline{E}_{P,t}$=Plan Average Exercise Calories (Cal/day) over time period t $N_0$=Plan Initial Normal Activity Calories (Cal/day) at time period t=0

$\overline{\rho}_{P,t}$=Plan Average Calorie Density (Cal/lb) over time period t $$k = \frac{\left(\frac{N_o}{W_0}\right)}{\overline{\rho}_{P,t}}\ (1/\text{day})$$

and:

$Adj_{Plan/Act,t}$ is an adjustment so that Calculated Plan Average Normal Activity Calories will be the same as Actual Average Normal Activity Calories.

4. The method of claim 1 wherein Step (a) comprises the further step of calculating the individual's Plan Average Calorie Deficit using the Plan Average Normal Activity Calories, Plan Average Exercise Calories and Plan Average Food Calories;

the Plan Average Calorie Deficit being calculated according to:

$$\overline{\text{Deficit}}_{P,t} = [\overline{N}_{P,t} + \overline{E}_{P,t} - \overline{F}_{P,t}]$$

where:

Deficits$_{P,t}$=Plan Average Calorie Deficit (Cal/day) over time t $\overline{N}_{P,t}$=Plan Average Normal Activity Calories (Cal/day) over time t $\overline{E}_{P,t}$=Plan Average Exercise Calories (Cal/day) over time t $\overline{F}_{P,t}$=Plan Average Food Calories (Cal/day) over time t and where deficits are defined to be positive.

5. The method of claim 1 wherein step (a) further comprises the step of calculating the individual's Plan Ending Weight comprising using the Plan Average Calorie Density;

$$W_{P,t} = W_o - \left( \frac{\overline{\text{Deficit}_{P,t}}}{\overline{\rho}_{P,t}} \right) t$$

$W_{P,t}$=Plan Ending Weight (lbs) at time period t
$W_0$=Beginning Actual Weight (lbs) at time period t=0
$(\overline{\text{Deficit}_{P,t}})$=Plan Average Calorie Deficit (Cal/day) over time period t
$\overline{\rho}_{P,t}$=Plan Average Calorie Density (Cal/lb) over time period t
the Plan Ending Weight being calculated according to.

6. The method of claim 1 wherein step (b) further comprises recording the Actual Date, Actual Food Calories and Actual Exercise Calories for each consecutive day.

7. The method of claim 1 wherein in step (c) the individual's Actual Normal Activity Calories is calculated exactly using the formulas:

$$N_{A,t} = \left[ \left( \frac{N_o}{xRMR} \right) + 6.25\Sigma(\Delta W_{A,t-1}) \right] xRMR \text{ for Males}$$

$$N_{A,t} = \left[ \left( \frac{N_o}{xRMR} \right) + 4.35\Sigma(\Delta W_{A,t-1}) \right] xRMR \text{ for Females}$$

where:

$N_{A,t}$=Actual Normal Activity Calories (Cal/day) at time period t
$N_0$=Plan Initial Normal Activity Calories (Cal/day) at time period t=0
xRMR=Plan Initial Normal Activity Calories Multiple of Resting Metabolic Rate (xRMR) at time period t=0
$\Delta W_{A,t-1}$=Change in Actual Forecast Weight (lbs) over time period t to t−1.

8. The method of claim 1, wherein in step (c) the individual's Actual Normal Activity Calories is calculated using the formula:

$$N_{A,t} = \left[ \left( \frac{N_o}{xRMR} \right) + 5.30\Sigma(\Delta W_{A,t-1}) \right] xRMR \text{ for Males or females}$$

where:

$N_{A,t}$=Actual Normal Activity Calories (Cal/day) at time period t
$N_0$=Plan Initial Normal Activity Calories (Cal/day) at time period t=0
xRMR=Plan Initial Normal Activity Calories Multiple of Resting Metabolic Rate (xRMR) at time period t=0
$\Delta W_{A,t-1}$=Change in Actual Forecast Weight (lbs) over time period t to t−1.

9. The method of claim 1 wherein in step (d) the individual's daily Actual Calorie Deficit is calculated according to the formula:

$$\text{Deficit}_{A,t} = [N_{A,t} + E_{A,t} - F_{A,t}]$$

where:
Deficit$_{A,t}$=Actual Calorie Deficit (Cal/day) at time t
$N_{A,t}$=Actual Normal Activity Calories (Cal/day) at time t
$E_{A,t}$=Actual Exercise Calories (Cal/day) at time t
$F_{A,t}$=Actual Food Calories (Cal/day) at time t
and where weight loss deficits are defined to be positive.

10. The method of claim 1 wherein in step (e) the individual's daily Actual Forecast Weight Change is calculated according to the formula:

$$\text{Daily Change}_{A,t} = -\left[ \frac{\text{Deficit}_{A,t}}{\overline{\rho}_{P/F,t}} \right]$$

where:
Daily Change$_{A,t}$=Actual Forecast Weight Change (lbs/day) at time period t
Deficit$_{A,t}$=Actual Calorie Deficit (Cal/day) at time period t
$\overline{\rho}_{P,t}$=Plan Average Calorie Density (Cal/lb) at time period t.

11. The method of claim 1 wherein in step (f) the individual's Actual Forecast Weight is calculated according to the formula:

$W_t = W_{t-1} + \text{Daily Change}_{A,t} \text{ if } W_{A,t} = 0$   (a)

$W_t = W_{A,t} + \text{Daily Change}_{A,t} \text{ if } W_{A,t} > 0$   (b)

where:
$W_t$=Actual Forecast Weight (lbs) at time period t
$W_{t-1}$=Actual Forecast Weight (lbs) at prior time period t−1
$W_{A,t}$=Actual Weight (lbs) at time period t
Daily Change$_{A,t}$=Actual Forecast Weight Change (lbs) at time t.

12. The method of claim 1 wherein in step (g) the individual's daily Plan Weight is calculated according to the formula:

$$W_{Plan,t} = W_o - \left( \frac{\text{Deficit}_{P/F,t} T}{\overline{\rho}_{P/F,t}} \right)$$

where:
$W_{Plan,t}$=Plan Weight (lbs) at time period t,120
$W_0$=Beginning Actual Weight (lbs) at time period t=0, 120
Deficit$_{P,t}$=Plan Deficit (Cal/day) at time period t,120
$\overline{\rho}_{P,t}$=Plan Average Calorie Density (Cal/lb) at time period t,120
T=Actual Days of Plan (Days) at time period t=T.

13. The method of claim 1 wherein in step (h) the individual's Actual Average Calorie Deficit calculated according to the formula:

$$\overline{\text{Deficit}_{A,t}} = [\overline{N}_{A,t} + \overline{E}_{A,t} - \overline{F}_{A,t}]$$

where:

$\overline{\text{Deficit}}_{A,t}$=Actual Average Calorie Deficit (Cal/day) over time t
$\overline{N}_{A,t}$=Actual Average Normal Activity Calories (Cal/day) over time t
$\overline{E}_{A,t}$=Actual Average Exercise Calories (Cal/day) over time t
$\overline{F}_{A,t}$=Actual Average Food Calories (Cal/day) over time t
and where deficits are defined to be positive.

14. The method of claim 1 wherein in step (i) the individual's Actual Average Calorie Density is calculated acccording to the formula:

$$\overline{\rho}_{A,t} = \frac{\Sigma \text{Deficit}_{A,t}}{\Sigma \Delta W_{A,t}}$$

where:
- $\overline{\rho}_{A,t}$=Actual Average Calorie Density (Cal/lb) over time period t
- $\Sigma \text{Deficit}_{A,t}$=Cumulative Actual Calorie Deficit (Cal) over time period t
- $\Sigma \Delta W_{A,t}$=Cumulative Actual Forecast Weight Change (lbs) over time period t where deficits and decreases in weight are defined to be positive.

15. The method of claim 14 wherein the accuracy of calories estimates are determined using the calculated Actual Average Calorie Density and the standard density of 3500 calories per pound of actual weight whereby Actual Average Calorie Densities of more than approximately 6000 calories per pound is evidence of inaccurate calorie estimates at a 95 percent confidence level.

16. The method of claim 14 wherein the Plan Ending Weight is predicted by replacing the Plan Average Calorie Density with the Actual Average Calorie Density.

17. The method of claim 14 wherein in step (k) the calculated Actual Days of Plan, the calculate Actual Average Food Calories, the calculated Actual Average Exercise Calories, the calculated Actual Average Normal Activity Calories and the calculated Actual Calorie Density are used with the Plan Number of Days, the Plan Average Food Calories, the Plan Average Exercise Calories, the Plan Average Normal Activity Calories and the Plan Average Calorie Density causing the Plan Ending Weight to equal the Actual Forecast Weight so as to initialize and equilibrate the plan and actual results for forecasting weight more accurately.

18. The method of claim 1 wherein an acceptable upper limit for the Plan Average Food Calories is calculated at a 95% confidence level so that weight will be lost over the Plan Number of Days, the Plan Average Food Calories being the sum of the Plan Average Normal Activity Calories and Plan Average Exercise Calories multiplied by 0.75.

19. The method of claim 1 wherein Step (k) further comprises graphing the individual's Actual Weight, Plan Weight, and Actual Forecast Weight and then identifying body water shifts, weight plateauing and resting metabolic rate changes.

20. The method of claim 1 wherein step (k) further comprises graphing the individual's Actual Weight, Plan Weight and Actual Forecast Weight to monitor results of purposefully made Plan changes.

* * * * *